United States Patent [19]

Boller et al.

[11] 4,062,798

[45] Dec. 13, 1977

[54] PHENYLPYRIMIDINE DERIVATIVES

[75] Inventors: Arthur Boller, Binningen; Marco Cereghetti, Basel; Hanspeter Scherrer, Therwil, all of Switzerland

[73] Assignee: Hoffmann-La Roche Inc., Nutley, N.J.

[21] Appl. No.: 719,018

[22] Filed: Aug. 30, 1976

[30] Foreign Application Priority Data

| Sept. 19, 1975 | Switzerland | 12235/75 |
| Jan. 9, 1976 | Switzerland | 221/76 |
| Feb. 25, 1976 | Switzerland | 2317/76 |
| July 30, 1976 | Switzerland | 9761/76 |

[51] Int. Cl.$^2$ .................... C09K 3/34; C02F 1/13; C07D 239/26; C07D 239/34; C07D 239/48
[52] U.S. Cl. .................... 252/299; 260/251 R; 260/463; 260/465 D; 260/465 E; 350/150; 350/160 LC
[58] Field of Search ............. 260/251 R, 463, 465 D, 260/465 E; 252/299; 350/160 LC, 150

[56] References Cited

U.S. PATENT DOCUMENTS

| 3,947,375 | 3/1976 | Gray et al. ............ 252/299 |
| 3,974,087 | 8/1976 | Gray et al. ............ 252/299 |
| 3,997,536 | 12/1976 | Boller et al. ............ 252/299 |

FOREIGN PATENT DOCUMENTS

| 2,257,588 | 6/1973 | Germany ............ 252/299 |

OTHER PUBLICATIONS

Zaschke; H., et al., J. Prakt. Chemie., vol. 315, No. 6, pp. 1113–1120 (1973).
Schubert; H., et al., J. Prakt Chemie., vol. 312, pp. 494–506 (1970).
Zaschke; H., J. Prakt. Chemie., vol. 317, No. 4, pp. 617–630 (1975).
Nash; J. A., et al., Mol. Cryst. Liq. Cryst., vol. 25, pp. 299–317 (1974).
Gray; G. W., et al., Liquid Crystals & Plastic Crystals, vol. 1, John Wiley & Sons, Inc., N.Y., pp. 103–125, 138–143 (1974).

*Primary Examiner*—Benjamin R. Padgett
*Assistant Examiner*—T. S. Gron
*Attorney, Agent, or Firm*—Samuel L. Welt; George M. Gould; William G. Isgro

[57] ABSTRACT

Compounds of the formula

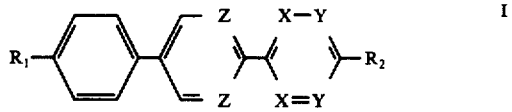

wherein when X is nitrogen, Y and Z are —CH—; or when Y is nitrogen, X and Z are —CH—; or when Z is nitrogen, X and Y are —CH—; and one of $R_1$ and $R_2$ is cyano and the other is straight-chain alkyl of 1 to 7 carbon atoms, straight-chain alkoxy of 1 to 7 carbon atoms or straight-chain alkanoyloxy of 2 to 7 carbon atoms, prepared by a variety of methods, are described. The compounds of the invention are useful as components of nematic mixtures.

49 Claims, No Drawings

PHENYLPYRIMIDINE DERIVATIVES

BRIEF SUMMARY OF THE INVENTION

The invention relates to compounds of the formula

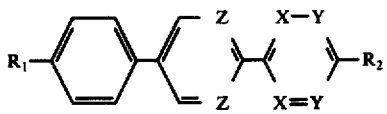

wherein when X is nitrogen, Y and Z are —CH—; or when Y is nitrogen, X and Z are —CH—; or when Z is nitrogen, X and Y are —CH—; and one of $R_1$ and $R_2$ is cyano and the other is straight-chain alkyl of 1 to 7 carbon atoms, straight-chain alkoxy of 1 to 7 carbon atoms or straight-chain alkanoyloxy of 2 to 7 carbon atoms, and their use as components of nematic mixtures.

DETAILED DESCRIPTION OF THE INVENTION

The compounds of the invention can be characterized by the formula

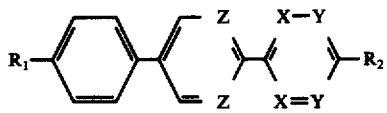

wherein when X is nitrogen, Y and Z are —CH—; or when Y is nitrogen, X and Z are —CH—; or when Z is nitrogen, X and Y are —CH—; and one of $R_1$ and $R_2$ is cyano and the other is straight-chain alkyl of 1 to 7 carbon atoms, straight-chain alkoxy of 1 to 7 carbon atoms or straight-chain alkanoyloxy of 2 to 7 carbon atoms.

The compounds of formula I are particularly useful as components of nematic mixtures in view of their liquid crystalline properties. The compounds of formula I possess, inter alia, a very high positive anisotropy of the dielectric constants ( $\epsilon_\parallel > \epsilon_\perp$, $\epsilon_\parallel$ denoting the dielectric constant along the longitudinal axis of the molecule and $\epsilon_\perp$ denoting the dielectric constant perpendicular thereto).

In an electric field, the compounds of formula I orientate themselves (because $\epsilon_\parallel > \epsilon_\perp$) with the direction of their largest dielectric constant, that is, with their longitudinal axes, parallel to the field direction. This effect is used, inter alia, in the interaction between embeded molecules and the liquid crystalline molecules (guest-host interaction) described by J. H. Heilmeier and L. A. Zanoni [Applied Physics Letters 13, 91 (1968)]. Another interesting application of the dielectric field orientation exists in the rotation cell discovered by M. Schadt and W. Helfrich [Applied Physics Letters 18, (1972)] and in the Kerr cell described in Molecular Crystals and Liquid Crystals 17, 355 (1972).

The electro-optical rotation cell comprises essentially a condenser with transparent electrodes, the dielectric of which is formed from a nematic crystal with $\epsilon_\parallel > \epsilon_\perp$. The longitudinal molecular axes of the liquid crystals are arranged spirally between the condenser plates in the fieldless state, the spiral structure is determined by the given wall orientation of the molecules. With the application of an electric potential to the condenser plates, the molecules adjust themselves with their longitudinal axes in the field direction, that is, perpendicular to the surface of the plates, whereby linearly polarized light is no longer rotated in the dielectric (the liquid crystal is uniaxially perpendicular to the surface of the plates). This effect is reversible and can be used to control electrically the optical transmissivity of the condenser.

In a "light rotation cell" of this type it is, inter alia, desirable to use compounds or mixtures which have a low threshold potential, a factor which is important, for example, when a rotation cell is used in clocks and the like.

It has now been found that the compounds of formula I of the invention have a particularly large mesophase range with high clearing points, due to which they are particularly suitable for the purpose of increasing the clearing points of nematic mixtures. In addition, they not only possess the required large positive anisotropy of the dielectric constants, and accordingly low threshold potentials in display devices based on a field effect, such as, for example, the rotation cell described in greater detail above, but they exhibit a short relay time and a high chemical stability. Furthermore, the compounds of formula I of the invention considerably improve, in display devices based on a field effect, the steepness of the optical transmission curves, as a function of the potential applied, when they are admixed with other nematic substances, such as, for example, paracyano-substituted Schiff's bases, esters or biphenyls. This property renders the compounds of formula I particularly valuable for multiplex working and for applications in display devices with a low threshold potential. Another advantage of the compounds of formula I of the invention is that they are colorless. Mixtures which contain the compounds of formula I of the invention are distinguished by their easy orientability and by the fact that they give a high contrast in display devices. Exemplary of the compounds of the invention are:

2-(4-Cyanophenyl)-5-(4-methylphenyl)-pyrimidine;
2-(4-Cyanophenyl)-5-(4-ethylphenyl)-pyrimidine;
2-(4-Cyanophenyl)-5-(4-n-propylphenyl)-pyrimidine;
2-(4-Cyanophenyl)-5-(4-n-butylphenyl)-pyrimidine;
2-(4-Cyanophenyl)-5-(4-n-pentylphenyl)-pyrimidine,
2-(4-Cyanophenyl)-5-(4-n-hexylphenyl)-pyrimidine;
2-(4-Cyanophenyl)-5-(4-n-heptylphenyl)-pyrimidine;
2-(4-Cyanophenyl)-5-(4-methoxyphenyl)-pyrimidine;
2-(4-Cyanophenyl)-5-(4-ethoxyphenyl)-pyrimidine;
2-(4-Cyanophenyl)-5-(4-n-propyloxyphenyl)-pyrimidine;
2-(4-Cyanophenyl)-5-(4-n-butyloxyphenyl)-pyrimidine;
2-(4-Cyanophenyl)-5-(4-n-pentyloxyphenyl)-pyrimidine;
2-(4-Cyanophenyl)-5-(4-n-hexyloxyphenyl)-pyrimidine;
2-(4-Cyanophenyl)-5-(4-n-heptyloxyphenyl)-pyrimidine;
2-(4-Cyanophenyl)-5-(4-acetoxyphenyl)-pyrimidine;
2-(4-Cyanophenyl)-5-(4-n-propionyloxyphenyl)-pyrimidine;
2-(4-Cyanophenyl)-5-(4-n-butyryloxyphenyl)-pyrimidine;
2-(4-Cyanophenyl)-5-(4-n-valeryloxyphenyl)-pyrimidine;
2-(4-Cyanophenyl)-5-(4-n-hexanoyloxyphenyl)-pyrimidine;
2-(4-Cyanophenyl)-5-(4-n-heptanoyloxyphenyl)-pyrimidine;

2-(4-Methylphenyl)-5-(4cyanophenyl)-pyrimidine;
2-(4-Ethylphenyl)-5-(4-cyanophenyl)-pyrimidine;
2-(4-n-Propylphenyl)-5-(4-cyanophenyl)-pyrimidine;
2-(4-n-Butylphenyl)-5-(4-cyanophenyl)-pyrimidine;
2-(4-n-Pentylphenyl)-5-(4-cyanophenyl)-pyrimidine;
2-(4-n-Hexylphenyl)-5-(4-cyanophenyl)-pyrimidine;
2-(4-n-Heptylphenyl)-5-(4-cyanophenyl)-pyrimidine;
2-(4-Methoxyphenyl)-5-(4-cyanophenyl)-pyrimidine;
2-(4-Ethoxyphenyl)-5-(4-cyanophenyl)-pyrimidine;
2-(4-n-Propyloxyphenyl)-5-(4-cyanophenyl)-pyrimidine;
2-(4-n-Butyloxphenyl)-5-(4-cyanophenyl)-pyrimidine;
2-(4-n-Pentyloxyphenyl)-5-(4-cyanophenyl)-pyrimidine;
2-(4-n-Hexyloxyphenyl)-5-(4-cyanophenyl)-pyrimidine;
2-(4-n-Heptyloxyphenyl)-5-(4-cyanophenyl)-pyrimidine;
2-(4-Acetoxyphenyl)-5-(4-cyanophenyl)-pyrimidine;
2-(4-n-Propionyloxyphenyl)-5-(4-cyanophenyl)-pyrimidine;
2-(4-n-Butyryloxyphenyl)-5-(4-cyanophenyl)-pyrimidine;
2-(4-n-Valeryloxyphenyl)-5-(4-cyanophenyl)-pyrimidine;
2-(4-Hexanoyloxyphenyl)-5-(4-cyanophenyl)-pyrimidine;
2-(4-n-Heptanoyloxyphenyl)-5-(4-cyanophenyl)-pyrimidine;
5-Methyl-2-(4'-cyano-4-biphenylyl)-pyrimidine;
5-Ethyl-2-(4'-cyano-4-biphenylyl)-pyrimidine;
5-n-Propyl-2-(4'-cyano-4-biphenylyl)-pyrimidine;
5-n-Butyl-2-(4'-cyano-4-biphenylyl)-pyrimidine;
5-n-Pentyl-2-(4'-cyano-4-biphenylyl)-pyrimidine;
5-n-Hexyl-2-(4'-cyano-4-cyano-4-biphenylyl)-pyrimidine;
5-n-Heptyl-2-(4'-cyano-4-biphenylyl)-pyrimidine;
5-Methoxy-2-(4'-cyano-4-biphenylyl)-pyrimidine;
5-Ethoxy-2-(4'-cyano-4-biphenylyl)-pyrimidine;
5-n-Propyloxy-2-(4'-cyano-4-biphenylyl)-pyrimidine;
5-n-Butyloxy-2-(4'-cyano-4-biphenylyl)-pyrimidine;
5-n-Pentyloxy-2-(4'-cyano-4-biphenylyl)-pyrimidine;
5-n-Hexyloxy-2-(4'-cyano-4-biphenylyl)-pyrimidine;
5-n-Heptyloxy-2-(4'-cyano-4-biphenylyl)-pyrimidine;
5-Acetoxy-2-(4'-cyano-4-biphenyl)-pyrimidine;
5-n-Propionyloxy-2-(4'-cyano-4-biphenyl)-pyrimidine;
5-n-Butyryloxy-2-(4'-cyano-4-biphenylyl)-pyrimidine;
5-n-Valeryloxy-2-(4'-cyano-4-biphenylyl)-pyrimidine;
5-n-Hexanoyloxy-2-(4'-cyano-4-biphenylyl)-pyrimidine;
5-n-Heptanoyloxy-2-(4'-cyano-4-biphenylyl)-pyrimidine;
2-Methyl-5-(4'-cyano-4-biphenylyl)-pyrimidine;
2-Ethyl-5-(4'-cyano-4-biphenylyl)-pyrimidine;
2-n-Propyl-5-(4'-cyano-4-biphenylyl)-pyrimidine;
2-n-Butyl-5 -(4'-cyano-4-biphenylyl)-pyrimidine;
2-n-Pentyl-5-(4'-cyano-4-biphenylyl)-pyrimidine;
2-n-Hexyl-5-(4'-cyano-4-biphenylyl)-pyrimidine;
2-n-Heptyl-5-(4'-cyano-4-biphenylyl)-pyrimidine;
2-Methoxy-5-(4'-cyano-4-biphenylyl)-pyrimidine;
2-Ethoxy-5-(4'-cyano-4-biphenylyl)-pyrimidine;
2-n-Propyloxy-5-(4'-cyano-4-biphenylyl)-pyrimidine;
2-n-Butyloxy-5-(4'-cyano-4-biphenylyl)-pyrimidine;
2-n-Pentyloxy-5-(4'-cyano-4-biphenylyl)-pyrimidine;
2-n-Hexyloxy-5-(4'-cyano-4-biphenylyl)-pyrimidine;
2-n-Heptyloxy-5-(4'-cyano-4-biphenylyl)-pyrimidine;
2-Acetoxy-5-(4'-cyano-4-biphenylyl)-pyrimidine;
2-n-Propionyloxy-5-(4'-cyano-4-biphenylyl)-pyrimidine;
2-n-Butyryloxy-5-(4'-cyano-4-biphenyl)-pyrimidine;
2-n-Valeryloxy-5-(4'-cyano-4-biphenylyl)-pyrimidine;
2-n-Hexanoyloxy-5-(4'-cyano-4-biphenylyl)-pyrimidine;
2-n-Heptanoyloxy-5-(4'-4-biphenylyl)-pyrimidine;
2-Cyano-5-(4'-methyl-4-biphenylyl)-pyrimidine;
2-Cyano-5-(4'-ethyl-4-biphenylyl)-primidine;
2-Cyano-5-(4'-n-propyl-4-biphenylyl)-pyrimidine;
2-Cyano-5-(4'-n-butyl-4-biphenylyl)-pyrimidine;
2-Cyano-5-(4'-n-pentyl-4-biphenylyl)-pyrimidine;
2-Cyano-5-(4'-n-hexyl-4-biphenylyl)-pyrimidine;
2-Cyano-5-(4'-n-heptyl-4-biphenylyl)-pyrimidine;
2-Cyano-5-(4'-methoxy-4-biphenylyl)-pyrimidine;
2-Cyano-5-(4'-ethoxy-4-biphenylyl)-pyrimidine;
2-Cyano-5-(4'-n-propyloxy-4-biphenylyl)-pyrimidine;
2-Cyano-5-(4'-n-butyloxy-4-biphenylyl)-pyrimidine;
2-Cyano-5-(4'-n-pentyloxy-4-biphenylyl)-pyrimidine;
2-Cyano-5-(4'-n-hexyloxy-4-biphenylyl)-pyrimidine;
2-Cyanno-5-(4'-n-heptyloxy-4-biphenylyl)-pyrimidine;
2-Cyano-5-(4'-acetoxy-4-biphenylyl)-pyrimidine;
2-Cyano-5-(4'-propionyloxy-4-biphenylyl)-pyrimidine;
2-Cyano-5-(4'-n-butyryloxy-4-biphenylyl)-pyrimidine;
2-Cyano-5-(4'-n-valeryloxy-4-biphenylyl)-pyrimidine;
2-Cyano-5-(4'-n-hexanoyloxy-4-biphenylyl)-pyrimidine;
2-Cyano-5-(4'-n-heptanoyloxy-4-biphenylyl)-pyrimidine;
5-Cyano-2-(4'-methyl-4-biphenylyl)-pyrimidine;
5-Cyano-2-(4'-ethyl-4-biphenylyl)-pyrimidine;
5-Cyano-2-(4'-n-propyl-4-biphenylyl)-pyrimidine;
5-Cyano-2-(4'-n-butyl-4-biphenylyl)-pyrimidine;
5-Cyano-2-(4'-n-pentyl-4-biphenylyl)-pyrimidine;
5-Cyano-2-(4'-n-hexyl-4-biphenylyl)-pyrimidine;
5-Cyano-2-(4'-n-heptyl-4-biphenylyl)-pyrimidine;
5-Cyano-2-(4'-methoxy-4-biphenylyl)-pyrimidine;
5-Cyano-2-(4'-ethoxy-4-biphenylyl)-pyrimidine;
5-Cyano-2-(4'-n-propyloxy-4-biphenylyl)-pyrimidine;
5-Cyano-2-(4'-n-butyloxy-4-biphenylyl)-pyrimidine;
5-Cyano-2-(4'-n-pentyloxy-4-biphenylyl)-pyrimidine;
5-Cyano-2-(4'-n-hexyloxy-4-biphenylyl)-pyrimidine;
5-Cyano-2-(4'-n-heptyloxy-4-biphenylyl)-pyrimidine;
5-Cyano-2-(4'-acetoxy-4-biphenylyl)-pyrimidine;
5-Cyano-2-(4'-n-propionyloxy-4-biphenylyl)-pyrimidine;
5-Cyano-2-(4'-n-butyryloxy-4-biphenylyl)-pyrimidine;
5-Cyano-2-(4'-n-valeryloxy-4-biphenylyl)-pyrimidine;
5-Cyano-2-(4'-n-hexanoyloxy-4-biphenylyl)-pyrimidine; and
5-Cyano-2-(4'-n-heptanoyloxy-4-biphenylyl)-pyrimidine.

Of the compounds of formula I, those wherein one of $R_1$ and $R_2$ is cyano and the other is straight-chain alkyl with 3 to 7 carbon atoms are preferred. In addition, compounds of formula I wherein Y is —CH— are also preferred. The compounds of formula I wherein Z is nitrogen and X and Y are —CH— are particularly preferred. Similarly, particularly preferred compounds of formula I are those wherein $R_2$ is cyano.

As can be seen from the above, those compounds of formula I wherein one of $R_1$ and $R_2$, preferably $R_2$, is cyano and the other is straight-chain alkyl of 3 to 7 carbon atoms and Z is nitrogen and X and Y are —CH— are particularly preferred.

Most preferred compounds of formula I are:
2-(4-cyanophenyl)-5-(4-n-butylphenyl)-pyrimidine; and
2-(4-cyanophenyl)-5-(4-n-hexylphenyl)-pyrimidine.

The compounds of formula I can be prepared in accordance with the invention as follows:

a. a compound of the formula

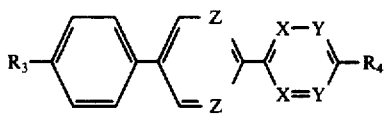

II wherein one of R$_3$ and R$_4$ is straight-chain alkyl of 1 to 7 carbon atoms, straight-chain alkoxy of 1 to 7 carbon atoms or straight-chain alkanoyloxy of 2 to 7 carbon atoms and the other is halogen, and X, Y and Z are as previously described, is reacted with copper-(I) cyanide or sodium or potassium cyanide, or b. in order to prepare compounds of formula I wherein Y is —CH—, R$_2$ is cyano and R$_1$, X and Z are as previously described, a compound of the formula

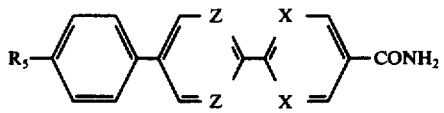

III wherein R$_5$ is straight-chain alkyl of 1 to 7 carbon atoms, straight-chain alkoxy of 1 to 7 carbon atoms or straight-chain alkanoyloxy of 2 to 7 carbon atoms and X and Z are as previously described, is dehydrated, or c. in order to prepare compounds of formula I wherein Y is nitrogen and R$_2$ is cyano and R$_1$, X and Z are as previously described, a compound of the formula

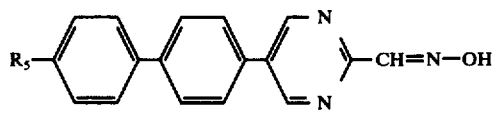

IV wherein R$_5$ is as previously described, is dehydrated.

In process embodiment (a) of the invention a compound of formula II is reacted with copper-(I) cyanide or sodium or potassium cyanide. The reaction is appropriately carried out in an inert organic solvent, such as, for example, ethylene glycol, tetrahydrofuran, dimethylformamide, dimethylsulfoxide, pyridine or acetonitrile. The temperature and pressure are not critical aspects in the reaction. For instance, atmospheric pressure and a temperature between room temperature and the boiling temperature of the reaction mixture are conveniently used. Preferably, the halogen in the compound of formula II is bromine.

The dehydration of a compound of formula III can be carried out with any suitable dehydrating agent, such as, for example, phosphorus oxychloride, phosphorus pentoxide, thionyl chloride or acetic anhydride. The dehydration can be effected in an inert organic solvent, such as, for example, a hydrocarbon or halogen hydrocarbon, if appropriate in the presence of a base, such as sodium acetate, pyridine or triethanolamine. However, it can also be carried out in the absence of an organic solvent. Conveniently, the reaction temperature is the reflux temperature of the reaction mixture. The pressure at which the reaction is carried out is not critical; advantageously, it is carried out at atmospheric pressure.

In another process embodiment of the invention, a compound of formula IV is dehydrated. The dehydration is conveniently effected by means of acetic anhydride or with anhydrous sodium acetate in glacial acetic acid. Conveniently, the reaction temperature is the reflux temperature of the reaction mixture. The pressure at which the reaction is carried out is not critical; advantageously, it is carried out at atmospheric pressure.

The preparation of the starting materials of formulas II, III and IV is illustrated by reaction schemes A to I, which follow, wherein "alkyl" is straight-chain alkyl of 1 to 7 carbon atoms, and wherein the reactions are exemplified with respect to compounds of formulas II, III and IV wherein one of R$_3$ and R$_4$ (or R$_5$) is straight-chain akyl of 1 to 7 carbon atoms and the other is bromine.

Throughout the specification, exemplary of alkyl are methyl, ethyl, propyl, butyl, pentyl, hexyl and heptyl. Exemplary of alkoxy are methoxy, ethoxy, propoxy, butoxy, pentoxy, hexyloxy and heptyloxy. Exemplary of alkanoyloxv are acetoxy, propionyloxy, butyryloxy, pentanoyloxy, hexanoyloxy and heptanoyloxy.

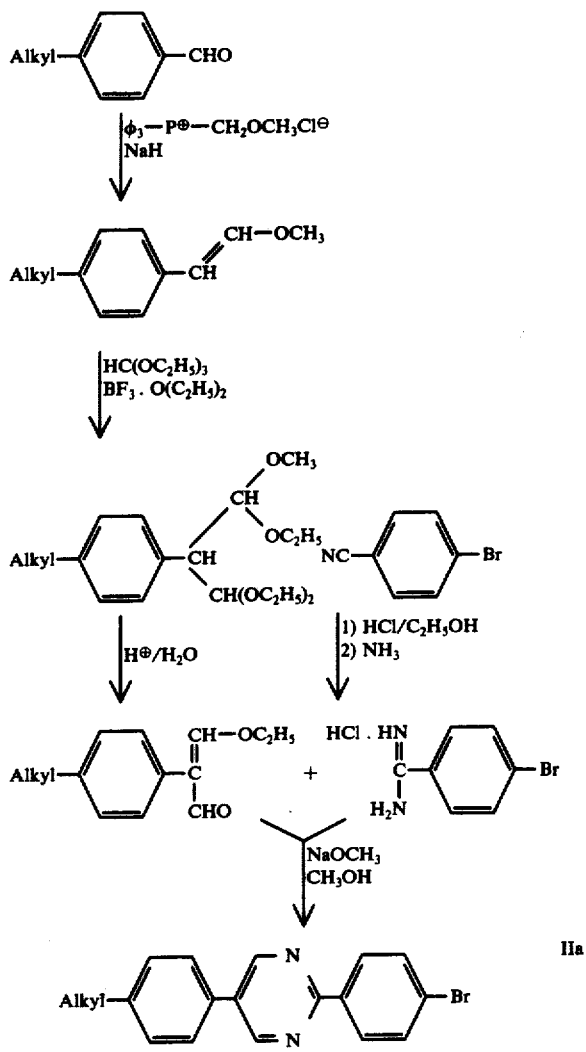

Scheme A

Scheme B
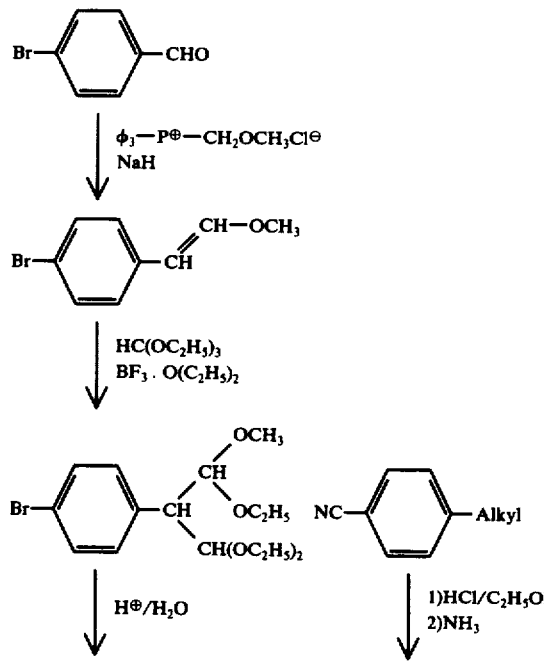
Scheme C
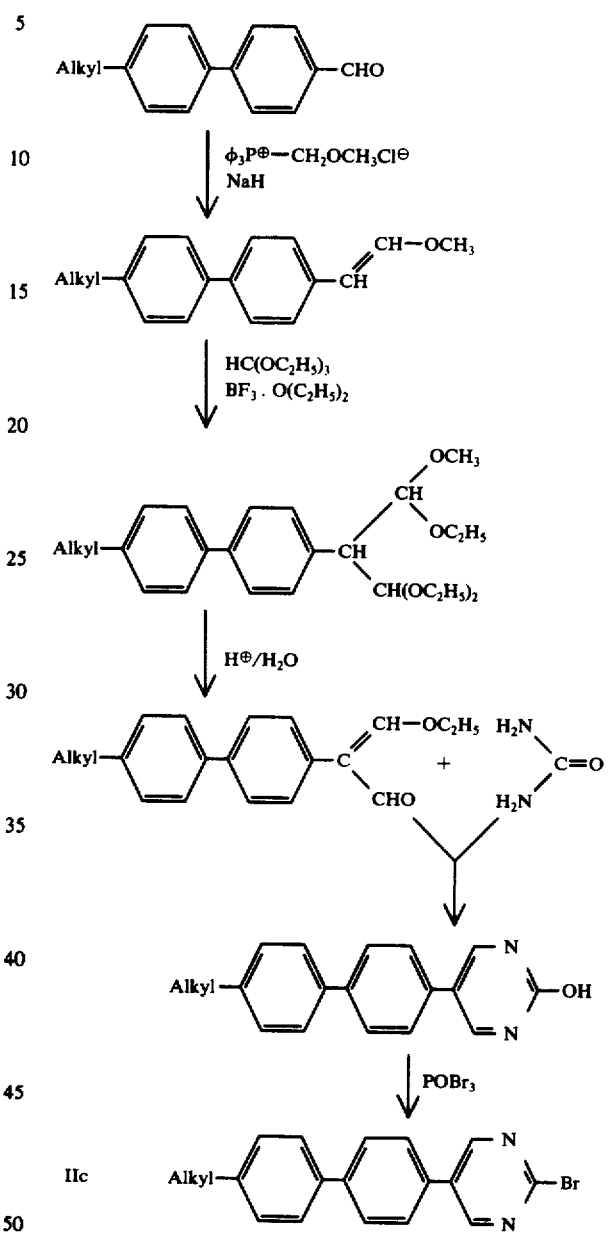
Scheme D
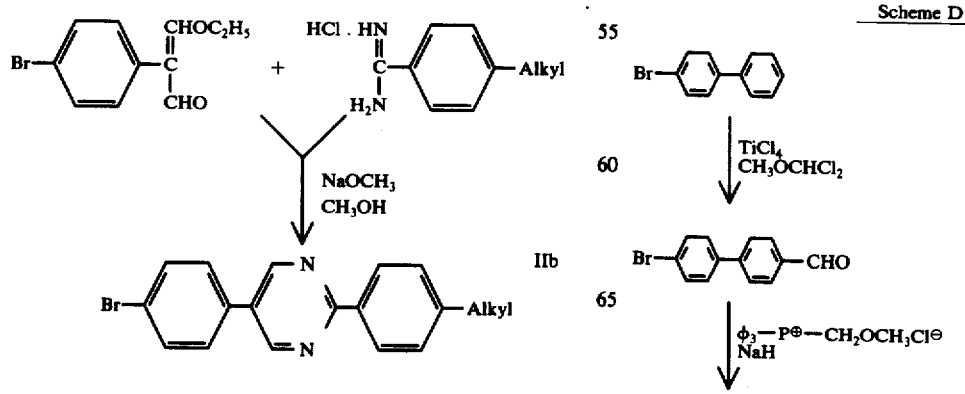

4,062,798
9
-continued
Scheme D
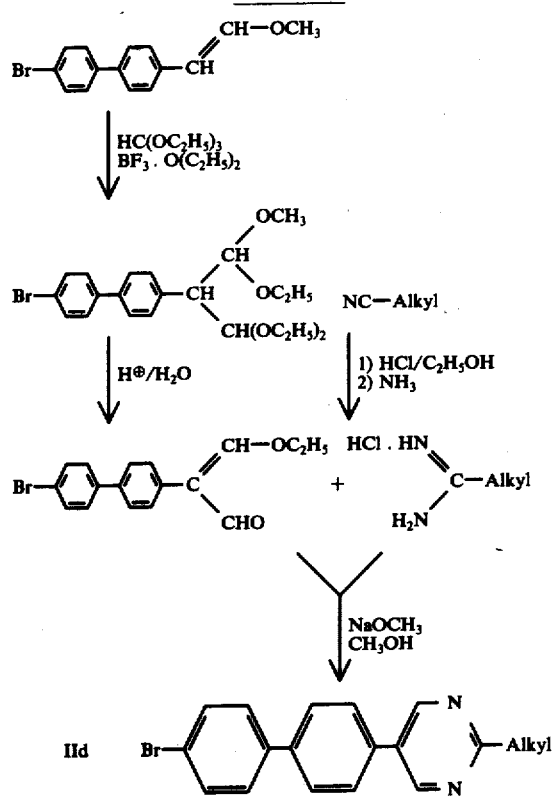
Scheme E
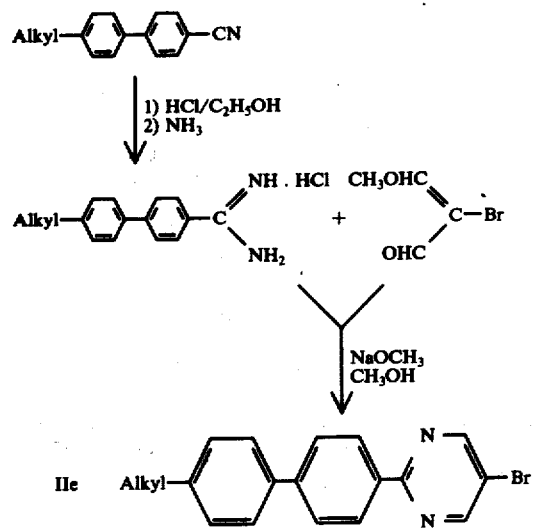
Scheme F
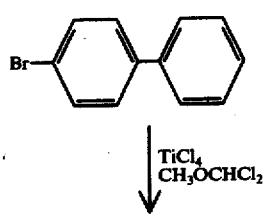
10
-continued
Scheme F
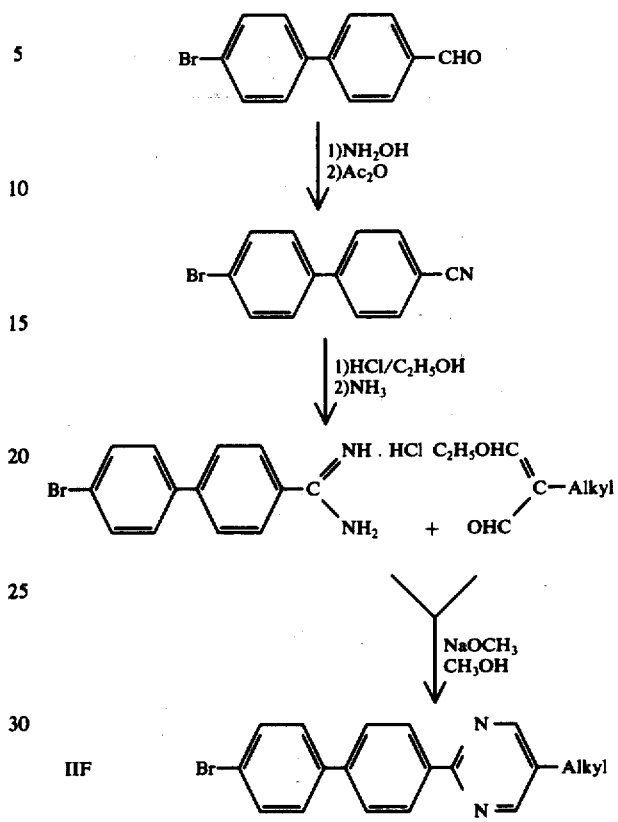
Scheme G
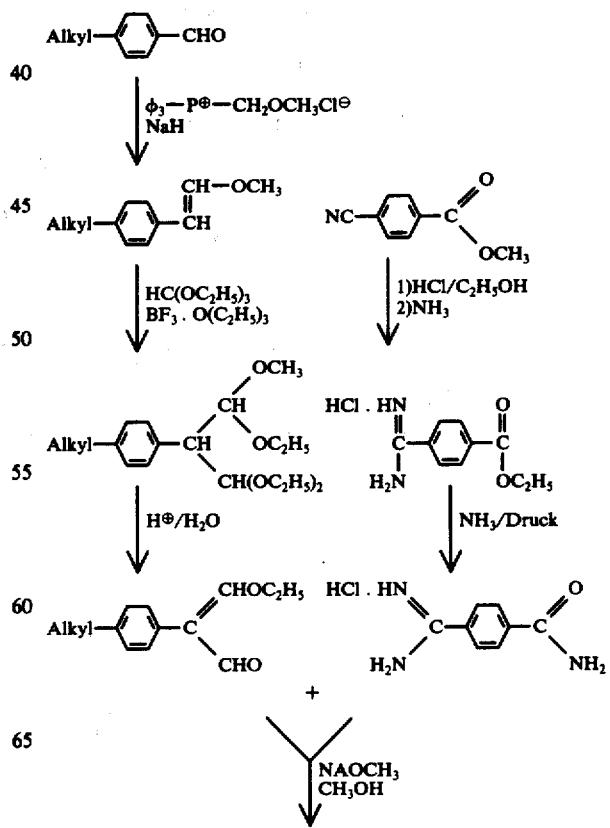

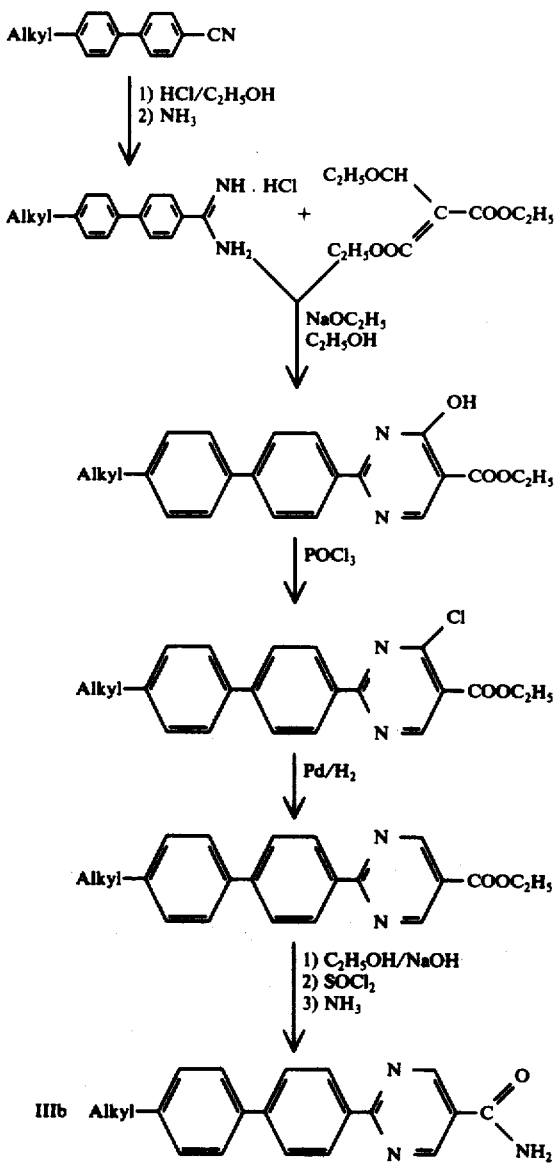
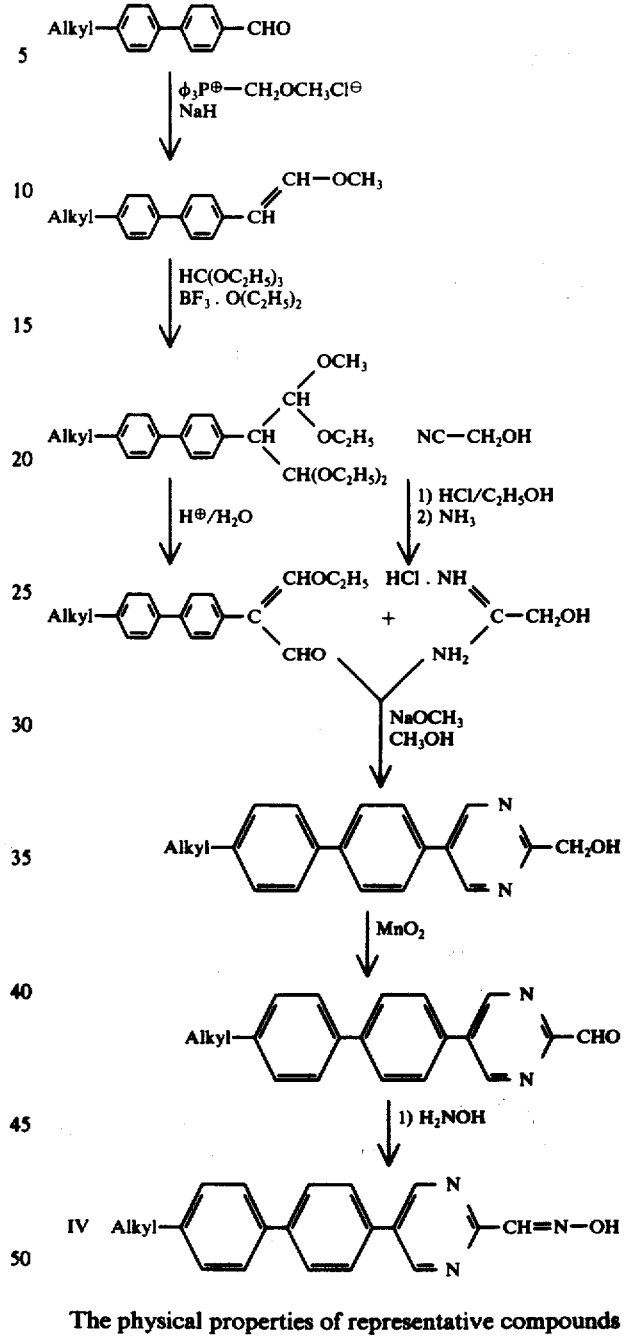

The physical properties of representative compounds of formula I of the invention are illustrated in the Table which follows:

Table

| $R_1$ | $R_2$ | X | Y | Z | M.P.[1] | Cl.P.[2] |
|---|---|---|---|---|---|---|
| $C_3H_7-$ | $-CN$ | $-CH-$ | $-CH-$ | $-N-$ | 154–154.5° | 261° |
| $C_4H_9-$ | $-CN$ | $-CH-$ | $-CH-$ | $-N-$ | 94° | 246–246.5° |
| $C_5H_{11}-$ | $-CN$ | $-CH-$ | $-CH-$ | $-N-$ | 125.5° | 242.5–243° |
| $C_6H_{13}-$ | $-CN$ | $-CH-$ | $-CH-$ | $-N-$ | 93° | 232.5° |
| $C_7H_{15}-$ | $-CN$ | $-CH-$ | $-CH-$ | $-N-$ | 104.5° | 226° |
| $-CN$ | $C_2H_5-$ | $-CH-$ | $-CH-$ | $-N-$ | 167–167.5° | 279–279.5° |
| $-CN$ | $C_3H_7-$ | $-CH-$ | $-CH-$ | $-N-$ | 167° | 278.5–279° |
| $-CN$ | $C_4H_9-$ | $-CH-$ | $-CH-$ | $-N-$ | 138.5° | 266–266.5° |
| $-CN$ | $C_5H_{11}-$ | $-CH-$ | $-CH-$ | $-N-$ | 131.5° | 262.5–263° |
| $-CN$ | $C_6H_{13}-$ | $-CH-$ | $-CH-$ | $-N-$ | 121.5° | 250° |
| $-CN$ | $C_7H_{15}-$ | $-CH-$ | $-CH-$ | $-N-$ | 121.5° | 245–245.5° |
| $-CN$ | $C_5H_{11}-$ | $-N-$ | $-CH-$ | $-CH-$ | 123.5–124° | 204.5–205° |
| $C_2H_5-$ | $-CN$ | $-N-$ | $-CH-$ | $-CH-$ | 166° | 241° |
| $C_6H_{13}-$ | $-CN$ | $-N-$ | $-CH-$ | $-CH-$ | 132.5° | 258.5–259.5° |
| $C_2H_5-$ | $-CN$ | $-N-$ | $-CH-$ | $-CH-$ | 166.3° | 240.9° |

Table-continued

| R₁ | R₂ | X | Y | Z | M.P.[1] | Cl.P.[2] |
|---|---|---|---|---|---|---|
| $C_3H_7$— | —CN | —N— | —CH— | —CH— | 138.7° | 232° |
| $C_4H_9$— | —CN | —N— | —CH— | —CH— | 129.3° | 274.6° |
| $C_2H_5$— | —CN | —CH— | —CH— | —N— | 182° | 262.2° |
| $C_3H_7O$— | —CN | —CH— | —CH— | —N— | 132° | 279.7° |
| $C_4H_9O$— | —CN | —CH— | —CH— | —N— | 119° | 271.6° |
| $C_5H_{11}O$— | —CN | —CH— | —CH— | —N— | 85.8° | 261° |
| $C_6H_{13}O$— | —CN | —CH— | —CH— | —N— | 94.8° | 254.3° |
| —CN | $C_3H_7$ | —N— | —CH— | —CH— | 125.6° | 275.7° |
| —CN | $C_4H_9$ | —N— | —CH— | —CH— | 112° | 262° |
| —CN | $C_6H_{13}$ | —N— | —CH— | —CH— | 108° | 245.5° |
| —CN | $C_7H_{15}$ | —N— | —CH— | —CH— | 110° | 241.5° |

[1]Melting Point
[2]Clearing Point

The compounds of formula I can be used in the form of their mixtures with other nematic substances, such as, for example, with one or more compounds of the formula

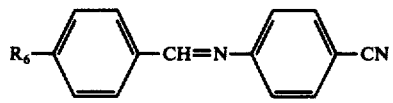

V wherein $R_6$ is straight-chain alkyl of 2 to 8 carbon atoms, straight-chain alkoxy of 4 to 7 carbon atoms, straight-chain alkanoyloxy of 2 to 8 carbon atoms or straight-chain alkyl carbonate of 2 to 11 carbon atoms, and/or with one or more compounds of the formula

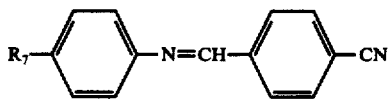

VI wherein $R_7$ is straight-chain alkyl of 4 to 7 carbon atoms or straight-chain alkyl carbonate of 2 to 11 carbon atoms, and/or with one or more compounds of the formula

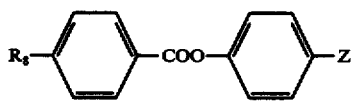

VII wherein Z is —CN, straight-chain alkyl of 1 to 9 carbon atoms, straight-chain alkoxy of 1 to 9 carbon atoms or straight-chain alkanoyloxy of 1 to 10 carbon atoms and $R_8$ is straight-chain alkyl of 4 to 8 carbon atoms, straight-chain alkoxy of 5 to 8 carbon atoms, straight-chain alkanoyloxy of 2 to 8 carbon atoms or straight-chain alkyl carbonate of 3 to 11 carbon atoms, and/or with one or more compounds of the formula

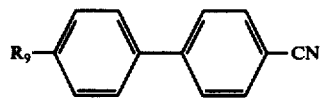

VIII wherein $R_9$ is straight-chain alkyl of 4 to 8 carbon atoms, straight-chain alkoxy of 4 to 8 carbon atoms, straight-chain alkanoyloxy of 4 to 9 carbon atoms or straight-chain alkyl carbonate of 4 to 11 carbon atoms, and/or with one or more trans-cinnamic acid esters of the formula

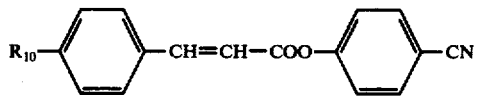

IX wherein $R_{10}$ is straight-chain alkyl of 1 to 8 carbon atoms, and/or with one or more compounds of the formula

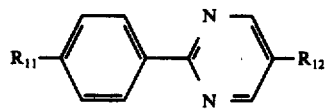

X wherein one of $R_{11}$ and $R_{12}$ is cyano and the other is straight-chain alkyl of 3 to 9 carbon atoms, straight-chain alkoxy of 2 to 9 carbon atoms or straight-chain alkanoyloxy of 2 to 9 carbon atoms, are used.

The compounds of formula X are new and can be prepared by dehydrating a compound of the formula

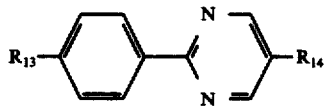

XI wherein one of $R_{13}$ and $R_{14}$ is straight-chain alkyl with 3 to 9 carbon atoms, straight-chain alkoxy of 2 to 9 carbon atoms or straight-chain alkanoyloxy of 2 to 9 carbon atoms, and the other is —$CONH_2$.

The preparation of the compounds of formula XI is illustrated by Reaction Schemes 1 and 2, which follow, wherein "alkyl" is straight-chain alkyl of 3 to 9 carbon atoms, and wherein the reactions are exemplified with respect to compounds of formulas II, III and IV, wherein one of $R_{13}$ and $R_{14}$ is straight-chain alkyl of 3 to 9 carbon atoms.

Scheme 1

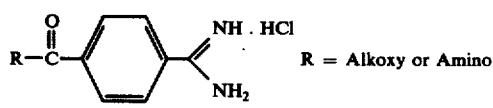

XIa

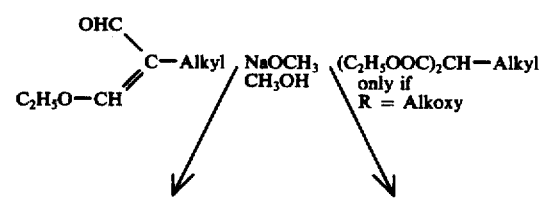

Scheme 1 -continued

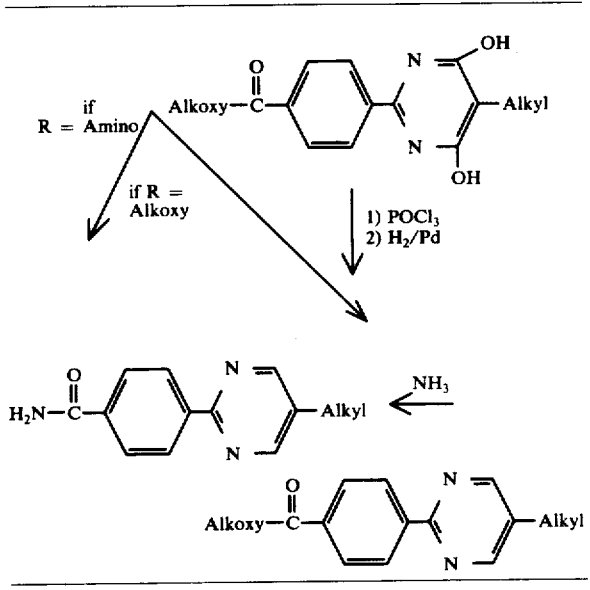

Scheme 2

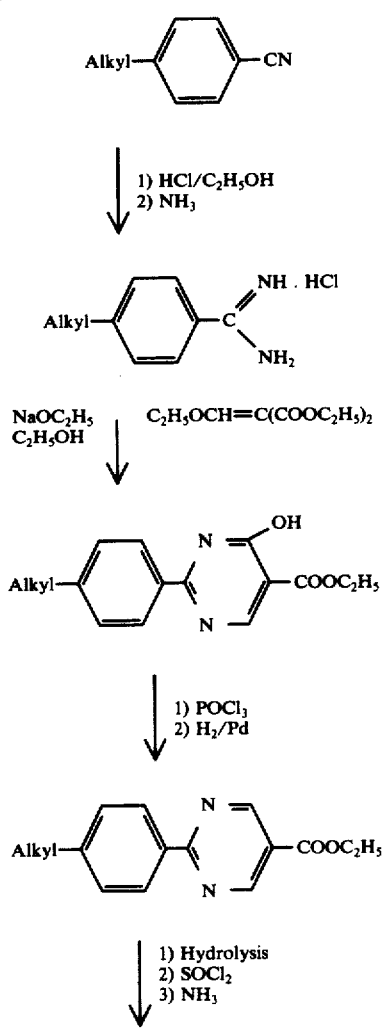

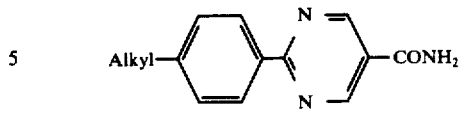

The compounds of formula I are utilized in nematic mixtures for electrooptical purposes in a weight ratio which preferably corresponds to their eutectic composition. However, the proportion of a compound of formula I in a nematic mixture is generally in the range of from about 0.5 to about 20 percent by weight and preferably is in the range of from about 2 to about 15 percent by weight.

The following mixtures are particularly preferred:

63.4% 4'-n-Pentyl-4-cyanobiphenyl, 31.6% 4'-n-heptyl-4-cyanobiphenyl and 5.0% 2-(4-cyanophenyl)-5-(4-n-hexylphenyl)-pyrimidine M.P. (Melting point) <3° C; Cl.p. (Clearing point) 47.4°–48.9° C.

57.0% 4'-n-Pentyl-4-cyanobiphenyl, 28.5% 4'-n-heptyl-4-cyanobiphenyl, 5% 5-cyano-2-(4-n-pentylphenyl)-pyrimidine, 5% 5-cyano-2-(4-n-hexylphenyl)-pyrimidine and 4.5% 2-(4-cyanophenyl)-5-(4-n-hexylphenyl)-pyrimidine M.p. <3° C; Cl.p. 53.2°–54.7° C.

44.2% 4'-Pentyl-4-cyanobiphenyl, 25.0% 4'-N-pentyloxy-4-cyanobiphenyl, 8.6% 5-n-hexyl-2-(4-cyanophenyl)pyrimidine, 11.4% 5-n-heptyl-2-(4-cyanophenyl)pyrimidine and 10.6% 2-(4-cyanophenyl)-5-(4-n-butylphenyl)-pyrimidine M.p. <0° C; Cl.p. 67.8°–68.9° C.

9.1% p-[(p-n-Propylbenzyliden)amino]benzonitrile, 26.6% p-[(p-n-butylbenzyliden)amino]benzonitrile, 24.0% p-[(p-n-pentylbenzyliden)amino]benzonitrile, 38% p-[(p-n-hexylbenzyliden)amino]benzonitrile and 2.3% 2-(4-cyanophenyl)-5-(4-n-propylphenyl)-pyrimidine M.p. <3° C; Cl.p. 70.3°–70.9° C.

8.9% p-[(p-n-Propylbenzyliden)amino]benzonitrile, 25.9% p-[(p-n-butylbenzyliden)amino]benzonitrile, 23.3% p-[(p-n-pentylbenzyliden)amino]benzonitrile, 36.9% p-[(p-n-hexylbenzyliden)amino]benzonitrile and 5.0% 2-(4-cyanophenyl)-5-(4-n-propylphenyl)-pyrimidine M.p. >3° C, <10° C; Cl.p. 75.3°–76.8° C.

11.0% p-[(p-n-Propylbenzyliden)amino]benzonitrile, 30.9% p-[(p-n-butylbenzyliden)amino]benzonitrile, 43.1% p-[(p-n-hexylbenzyliden)amino]benzonitrile, 12.4% 5-n-heptyl-2-(4-cyanophenyl)-pyrimidine and 2.3% 2-(4-cyanophenyl)-5-(4-n-propylphenyl)-pyrimidine M.p. <0° C; Cl.p. 65.8°–66.4° C.

10.4% p-[(p-n-Propylbenzyliden)amino]benzonitrile, 29.5% p-[(p-n-Butylbenzyliden)amino]benzontrile, 41.5% p-[(p-n-hexylbenzyliden)amino]benzonitrile, 7.4% p-n-heptylbenzoic acid p'-cyanophenyl ester and 10.7% 2-(4-cyanophenyl)-5-(4-n-butylphenyl)-pyrimidine M.p. <0° C; Cl.p. 81.2°–82.2° C.

49.3% p-[(p-n-Propylbenzyliden)amino]benzonitrile, 12.1% 5-n-hexyl-2-(4-cyanophenyl)-pyrimidine, 16.1% 5-n-heptyl-2-(4-cyanophenyl)-pyrimidine, 13.2% 2-(4-cyanophenyl)-5-(4-n-butylphenyl)-pyrimidine and 9.0% 2-(4-cyanophenyl)-5-(4-n-hexylphenyl)-pyrimidine M.p. <0° C; Cl.p. 96.8°–97.9° C.

6.3% p-n-Butylbenzoic acid p'-cyanophenyl ester, 8.0% p-n-hexylbenzoic acid p'-cyanophenyl ester, 11.5% p-[(p-n-propylbenzyliden)amino]benzonitrile, 31.9% p-[(p-n-butylbenzyliden)amino]benzonitrile, 11.6% 2-(4-cyanophenyl)-5-(4-butylphenyl)-pyrimidine, 7.0% 2-(4-cyanophenyl)-5-(4-n-pentylphenyl)-pyrimidine, 9.8% 2-(4-cyanophenyl)-5-(4-n-hexylphenyl)pyrimidine and 13.1% 2-(4-cyanophenyl)-5-(4-n-heptylphenyl)-pyrimidine M.p. <0° C; Cl.p. 77.9° C.

11.5% p-[(p-n-Propylbenzyliden)amino]benzonitrile, 31.9% p-[(p-n-butylbenzyliden)amino]benzonitrile, 6.3% p-n-butylbenzoic acid p'-cyanophenyl ester, 8.0% p-n-hexylbenzoic acid p'-cyanophenyl ester, 7.0% 5-n-pentyl-2-(4-cyanophenyl)-pyrimidine, 9.8% 5-n-hexyl-2-(4-cyanophenyl)-pyrimidine, 13.1% 5-n-heptyl-2-(4-cyanophenyl)-pyrimidine and 11.6% 2-(4-cyanophenyl)-5-(4-n-butylphenyl)-pyrimidine M.p. <0° C; Cl.p. 77.5° C.

13.0% p-[(p-n-Propylbenyliden)amino]benzonitrile, 35.2% p-[(p-n-butylbenzyliden)amino]benzonitrile, 7.4% p-n-butylbenzoic acid p'-cyanophenyl ester, 7.8% p-n-pentylbenzoic acid p'-cyanophenyl ester, 9.6% p-n-hexylbenzoic acid p'-cyanophenyl ester, 8.1% 5-n-pentyl-2-(4-cyanophenyl)-pyrimidine, 15.2% 5-n-heptyl-2-(4-cyanophenyl)-pyrimidine and 2.6% 2-(4-cyanophenyl)-5-(4-n-propylphenyl)-pyrimidine M.p. <0° C; Cl.p. 62.5° C.

12.5% p-[(p-n-Propylbenzyliden)amino]benzonitrile, 34.3% p-[(p-n-butylbenzyliden)amino]benzontrile, 7.0% p-n-butylbenzoic acid p'-cyanophenyl ester, 8.7% p-n-hexylbenzoic acid p'-cyanophenyl ester, 9.7% p-n-heptylbenzoic acid p'-cyanophenyl ester, 7.5% 5-n-pentyl-2-(4-cyanophenyl)-pyrimidine, 14.0% 5-n-heptyl-2-(4-cyanophenyl)-pyrimidine, 2.5% 2-(4-cyanophenyl)-5-(4-n-propylphenyl)-pyrimidine and 3.6% p-[(p-ethoxybenzyliden)amino]benzonitrile M.p. <0° C; Cl.p. 65.0° C.

36.0% p-[(p-n-Butylbenzyliden)amino]benzonitrile, 7.7% p-n-butylbenzoic acid p'-cyanophenyl ester, 8.1% p-n-pentylbenzoic acid p'-cyanophenyl ester, 10.0% p-n-hexyobenzoic acid p'-cyanophenyl ester, 8.4% 5-n-pentyl-2-(4-cyanophenyl)-pyrimidine, 15.8% 5-n-heptyl-2-(4-cyanophenyl)-pyrimidine and 13.0% 2-(4-cyanophenyl)-5-(4-n-butylphenyl)-pyrimidine M.p. <0° C; Cl.p. 81.0° C.

16.8% p-[(p-n-Propylbenzyliden)amino]benzonitrile, 10.2% p-n-butylbenzoic acid p'-cyanophenyl ester, 11.0% p-n-pentylbenzoic acid p'-cyanophenyl ester, 14.1% p-n-hexylbenzoic acid p'-cyanophenyl ester, 10.9% 5-n-pentyl-2-(4-cyanophenyl)-pyrimidine, 21.0% 5-n-heptyl-2-(4-cyanophenyl)-pyrimidine and 15.5% 2-(4-cyanophenyl)-5-(4-n-butylphenyl)-pyrimidine M.p. <10° C; Cl.p. 85.5° C.

16.2% p-[(p-n-Propylbenzyliden)amino]benzonitrile, 9.7% p-n-butylbenzoic acid p'-cyanophenyl ester, 13.4% p-n-hexylbenzoic acid p'-cyanophenyl ester, 14.4% p-n-heptylbenzoic acid p'-cyanophenyl ester, 10.5% 5-n-pentyl-2-(4-cyanophenyl)-pyrimidine. 20.2% 5-n-heptyl-2-(4-cyanophenyl)-pyrimidine and 15.1% 2-(4-cyanophenyl)-5-(4-n-butylphenyl)-pyrimidine M.p. <10° C; Cl.p. 83.5° C.

11.6% p-[(p-n-Propylbenzyliden)amino]benzonitrile, 32.1% p-[(p-n-butylbenzyliden)amino]benzonitrile, 6.4% p-n-butylbenzoic acid p'-cyanophenyl ester, 8.1% p-n-hexylbenzoic acid p'-cyanophenyl ester, 8.7% p-n-hepthylbenzoic acid p'-cyanophenyl ester, 7.1% 5-n-pentyl-2-(4-cyanophenyl)-pyrimidine, 13.2% 5-n-heptyl-2-(4-cyanophenyl)-pyrimidine and 11.7% 2-(4-cyanophenyl)-5-(4-n-butylphenyl)-pyrimidine M.p. <0° C; Cl.p. 80.0° C.

10.3% p-n-Butylbenzoic acid p'-cyanophenyl ester, 11.1% p-n-pentylbenzoic acid p'-cyanophenyl ester, 14.3% p-n-hexylbenzoic acid p'-cyanophenyl ester, 15.4% p-n-heptylbenzoic acid p'-cyanophenyl ester, 11.0% 5-n-pentyl-2-(4-cyanophenyl)-pyrimidine, 21.2% 5-n-heptyl-2-(4-cyanophenyl)-pyrimidine and 15.6% 2-(4-cyanophenyl)-5-(4-n-butylphenyl)-pyrimidine M.p. <10° C; Cl.p. 82.5° C.

10.0% p-n-Butylbenzoic acid p'-cyanophenyl ester, 10.9% p-n-pentylbenzoic acid p'-cyanophenyl ester, 13.4% p-n-hexylbenzoic acid p'-cyanophenyl ester, 14.9% p-n-heptylbenzoic acid p'-cyanophenyl ester, 10.5% 5-n-pentyl-2-(4-cyanophenyl)-pyrimidine, 20.6% 5-n-heptyl-2-(4-cyanophenyl)-pyrimidine, 3.3% 2-(4-cyanophenyl)-5-(4-n-propylphenyl)-pyrimidine and 15.5% 2-(4-cyanophenyl)-5-(4-n-butylphenyl)-pyrimidine M.p. <10° C; Cl.p. 88.5° C.

44.5% p-[(p-n-Hexylbenzyliden)amino]benzonitrile, 6.6% p-n-butylbenzoic acid p'-cyanophenyl ester, 6.9% p-n-pentylbenzoic acid p'-cyanophenyl ester, 8.4% p-n-hexylbenzoic acid p'-cyanophenyl ester, 7.3% 5-n-pentyl-2-(4-cyanophenyl)pyrimidine, 13.6% 5-n-heptyl-2-(4-cyanophenyl)-pyrimidine and 11.9% 2-(4-cyanophenyl)-5-(4-n-butylphenyl)-pyrimidine M.p. <0° C; Cl.p. 80.0° C.

15.3% p-[(p-n-Propylbenzyliden)amino]benzonitrile, 9.0% p-n-butylbenzoic acid p'-cyanophenyl ester, 9.9% p-n-pentylbenzoic acid p'-cyanophenyl ester, 12.8% p-n-hexylbenzoic acid p'-cyanophenyl ester, 9.2% 5-n-pentyl-2-(4-cyanophenyl)pyrimidine, 12.7% 5-n-hexyl-2-(4-cyanophenyl)-pyrimidine, 18.2% 5-n-heptyl-2-(4-cyanophenyl)-pyrimidine and 12.9% 2-(4-cyanophenyl)-5-(4-n-butylphenyl)pyrimidine M.p. <3° C; Cl.p. 79.0° C.

18.1% p-n-Butylbenzoic acid p'-cyanophenyl ester, 13.3% p-n-hexylbenzoic acid p'-cyanophenyl ester, 8.4% p-n-octylbenzoic acid p'-cyanophenyl ester, 10.4% 5-n-pentyl-2-(4-cyanophenyl)-pyrimidine, 14.8% 5-n-hexyl-2-(4-cyanophenyl)-pyrimidine, 19.8% 5-n-heptyl-2-(4-cyanophenyl)-pyrimidine and 15.0% 2-(4-cyanophenyl)-5-(4-n-butylphenyl)-pyrimidine M.p. <10° C; Cl.p. 78.5° C.

42.4% p-[(p-n-Butylbenzyliden)amino]benzonitrile, 6.0% p-n-butylbenzoic acid p'-cyanophenyl ester, 7.5% p-n-hexylbenzoic acid p'-cyanophenyl ester, 4.2% p-n-octylbenzoic acid p'-cyanophenyl ester, 6.7% 5-n-penyl-2-(4-cyanophenyl)-pyrimidine, 9.3% 5-n-hexyl-2-(4-cyanophenyl)-pyrimidine, 12.3% 5-n-heptyl-2-(4-cyanophenyl)-pyrimidine and 11.2% 2-(4-cyanophenyl)-5-(4-n-butylphenyl)-pyrimidine M.p. <0° C; Cl.p. 76.0° C.

10.1% p-n-Butylbenzoic acid p'-cyanophenyl ester, 12.0% p-n-pentylbenzoic acid p'-cyanophenyl ester, 14.2% p-n-hexylbenzoic acid p'-cyanophenyl ester, 15.2% p-n-heptylbenzoic acid p'-cyanophenyl ester, 11.1% 5-N-pentyl-2-(4-cyanophenyl)-pyrimidine, 21.3% 5-n-heptyl-2-(4-cyanophenyl)-pyrimidine and 16.0% 2-(4-cyanophenyl)-5-(4-n-butylphenyl)-pyrimidine M.p. <3° C; Cl.p. 82.0° C.

33.1% p-[(p-n-Butylbenzyliden)amino]benzonitrile, 6.7% p-n-butylbenzoic acid p'-cyanophenyl ester, 7.1% p-n-pentylbenzoic acid p'-cyanophenyl ester, 8.6% p-n-hexylbenzoic acid p'-cyanophenyl ester, 7.4% 5-n-pentyl-2-(4-cyanophenyl)-pyrimidine, 10.4% 5-n-hexyl-2-(4-cyanophenyl)-pyrimidine, 13.9% 5-n-heptyl-2-(4-cyanophenyl)-pyrimidine and 12.0% 2-(4-cyanophenyl)-5-(4-n-butylphenyl)-pyrimidine M.p. <0° C; Cl.p. 76.8° C.

7.7% p-[(p-n-Propylbenzyliden)amino]benzonitrile, 23.2% p-[(p-n-butylbenzyliden)amino]benzonitrile, 34.2% p-[(p-n-hexylbenzyliden)amino]benzonitrile, 11.1% 5-cyano-2-(4-n-hexylphenyl)-pyrimidine, 7.9% 5-n-heptyl-2-(4-cyanophenyl)-pyrimidine, 1.6% 2-(4-cyanophenyl)-5-(4-n-propylphenyl)-pyrimidine, 8.5% 2-(4-cyanophenyl)-5-(4-n-butylphenyl)-pyrimidine and 5.3% 2-(4-cyanophenyl)-5-(4-n-hexylphenyl)-pyrimidine M.p. <0° C; Cl.p. 93.5° C.

10.1% p-[(p-n-Propylbenzyliden)amino]benzonitrile, 29.0% p-[(p-n-butylbenzyliden)amino]benzonitrile, 40.8% p-[(p-n-hexylbenzyliden)amino]benzonitrile, 2.0% 2-(4-cyanophenyl)-5-(4-n-propylphenyl)-pyrimidine, 10.6% 2-(4-cyanophenyl)-5-(4-n-butylphenyl)-pyrimidine and 7.3% 4-cyano-4''-n-pentyl-p-terphenyl M.p. <0° C; Cl.p. 101° C.

9.8% p-[(p-n-Propylbenzyliden)amino]benzonitrile, 28.2% p-[(p-n-butylbenzyliden)amino]benzonitrile, 39.9% p-[(p-n-hexylbenzyliden)amino]benzonitrile, 11.4% 5-cyano-2-(4'-n-hexyl-4-biphenylyl)-pyrimidine and 10.4% 2-(4-cyanophenyl)-5-(4-n-butylphenyl)-pyrimidine M.p. <0° C; Cl.p. 109° C.

10.3% p-[(p-n-Propylbenzyliden)amino]benzonitrile, 29.4% p-[(p-n-butylbenzyliden)amino]benzonitrile, 40.9% p-[(p-n-hexylbenzyliden)amino]benzonitrile, 5.8% 5-cyano-2-(4'-n-propyl-4-biphenylyl)-pyrimidine, 10.7% 2-(4-cyanophenyl)-5-(4-n-butylphenyl)-pyrimidine and 2.2% 5-n-pentyl-2-(4'-cyano-4-biphenylyl)-pyrimidine M.p. <0° C; Cl.p. 102° C.

9.0% p-[(p-n-(Propylbenzyliden)amino]benzonitrile, 27.3% p-[(p-n-butylbenzyliden)amino]benzonitrile, 41.9% p-[(p-n-hexylbenzyliden)amino]benzonitrile, 6.8% 5-cyano-2-(4'-n-hexyl-4-biphenylyl)-pyrimidine, 10.1% 2-(4-cyanophenyl)-5-(4-n-butylphenyl)-pyrimidine and 4.9% 2-(4-cyanophenyl)-5-(4-n-hexylphenyl)-pyrimidine M.p. <0° C; Cl.p. 106° C.

16.0% p-[(p-n-Propylbenzyliden)amino]benzonitrile, 64.2% p-[(p-n-hexylbenzyliden)amino]benzonitrile, 3.7% 5-cyano-2-(4-n-butyryloxyphenyl)-pyrimidine, 2.6% 5-cyano-2-(4-n-valeryloxyphenyl)-pyrimidine, 2.2% 2-(4-cyanophenyl)-5-(4-n-propylphenyl)-pyrimidine and 11.2% 2-(4-cyanophenyl)-5-(4-n-butylphenyl)-pyrimidine M.p. <0° C; Cl.p. 92.0° C.

11.1% p-[(p-n-Propylbenzyliden)amino]benzonitrile, 31.3% p-[(p-n-butylbenzyliden)amino]benzonitrile, 43.5% p-[(p-n-hexylbenzyliden)amino]benzonitrile, 2.4% 2-(4-cyanophenyl)-5-(4-n-propylphenyl)-pyrimidine and 11.4% 2-(4-cyanophenyl)-5-(4-n-butylphenyl)-pyrimidine M.p. <0° C; Cl.p. 88.0° C.

10.0% p-[(p-n-Propylbenzyliden)-amino]benzonitrile, 28.6% p-[(p-n-butylbenzyliden)amino]benzonitrile, 40.6% p-[(p-n-hexylbenzyliden)amino]benzonitrile, 4.9% 5-cyano-2-(4-n-butyryloxyphenyl)-pyrimidine, 3.0% 5-cyano-2-(4-n-valeryloxyphenyl)-pyrimidine, 2.0% 2-(4-cyanophenyl)-5-(4-n-propylphenyl)pyrimidine and 10.5% 2-(4-cyanophenyl)-5-(4-n-butylphenyl)-pyrimidine M.p. <0° C; Cl.p. 90.0° C.

9.1% p-[(p-n-Propylbenzyliden)amino]benzonitrile, 26.8% p-[(p-n-butylbenzyliden)amino]benzonitrile, 38.3% p-[(p-n-hexylbenzyliden)amino]benzonitrile, 6.4% 5-cyano-2-(4-n-pentylphenyl)-pyrimidine, 4.6% 5-cyano-2-(4-n-butyloxyphenyl)-pyrimidine, 2.7% 5-cyano-2-(4-n-valeryloxyphenyl)-pyrimidine, 1.8% 2-(4-cyanophenyl)-5-(4-n-propylphenyl)-pyrimidine and 9.8% 2-(4-cyanophenyl)-5-(4-butylphenyl)-pyrimidine M.p. <0° C; Cl.p. 91.5° C.

11.3% p-[(p-n-Propylbenzyliden)amino]benzonitrile, 31.5% p-[(p-n-butylbenzyliden)amino]benzonitrile, 43.2% p-[(p-n-hexylbenzyliden)amino]benzonitrile, 11.5% 2-(4-cyanophenyl)-5-(4-n-butylphenyl)-pyrimidine and 2.5% 5-n-pentyl-2-(4'-cyano-4-biphenylyl)-pyrimidine M.p. <0° C; Cl.p. 87.0° C.

8.8% p-[(p-n-Propylbenzyliden)amino]benzonitrile, 25.9% p-[(p-n-butylbenzyliden)amino]benzonitrile, 36.9% p-[(p-n-hexylbenzyliden)amino]benzonitrile, 7.4% 5-n-hexyl-2-(4-cyanophenyl)-pyrimidine, 9.4% 5-n-heptyl-2-(4-cyanophenyl)pyrimidine, 9.5% 2-(4-cyanophenyl)-5-(4-n-butylphenyl)-pyrimidine and 1.9% 5-n-pentyl-2-(4'-cyano-4-biphenylyl)-pyrimidine M.p. <0° C; Cl.p. 81.0° C.

11.0% p-[(p-n-Propylbenzyliden)amino]benzonitrile, 30.8% p-[(p-n-butylbenzyliden)amino]benzonitrile, 42.4% p-[(p-n-hexylbenzyliden)amino]benzonitrile, 2.2% 2-(4-cyanophenyl)-5-(4-n-propylphenyl)-pyrimidine, 11.2% 2-(4-cyanophenyl)-5-(4-n-butylphenyl)-pyrimidine and 2.4% 5-n-pentyl-2-(4'-cyano-4-biphenylyl)-pyrimidine m.p. <0° C; Cl.P. 92.5° C.

17.8% p-[(p-n-Propylbenzyliden)amino]benzonitrile, 57.8% p-[(p-n-hexylbenzyliden)amino]benzonitrile, 3.6% 2-(4-cyanophenyl)-5-(4-n-propylphenyl)-pyrimidine, 16.2% 2-(4-cyanophenyl)-5-(4-n-butylphenyl)-pyrimidine and 4.1% 5-n-pentyl- 2-(4'-cyano-4-biphenylyl)-pyrimidine M.p. <10° C; Cl.p. 107.5° C.

14.7% p-[(p-n-Propylbenzyliden)amino]benzonitrile, 51.2% p-[(p-n-hexylbenzyliden)amino]benzonitrile, 13.3% 5-n-hexyl-2-(4-cyanophenyl)-pyrimidine, 3.0% 2-(4-cyanophenyl)-5-(4-n-propylphenyl)-pyrimidine, 14.0% 2-(4-cyanophenyl)-5-(4-n-butylphenyl)-pyrimidine and 3.3% 5-n-pentyl-2-(4'-cyano-4-biphenylyl)-pyrimidine M.p. <3° C; Cl.p. 97.5° C.

10.2% p-[(p-n-Propylbenzyliden)amino]benzonitrile, 29.1% p-[(p-n-butylbenzyliden)amino]benzonitrile, 40.6% p-[(p-n-hexylbenzyliden)amino]benzonitrile, 10.6% 2-(4-cyanophenyl)-5-(4-n-butylphenyl)-pyrimidine, 6.9% 2-(4-cyanophenyl)-5-(4-n-hexylphenyl)-pyrimidine and 2.1% 5-n-pentyl-2-(4'-cyano-4-biphenylyl)-pyrimidine M.p. <0° C; Cl.p. 99.0° C.

11.3% p-[(p-n-Propylbenzyliden)amino]benzonitrile, 31.5% p-[(p-n-butylbenzyliden)amino]benzonitrile, 43.2% p-[(p-n-hexylbenzyliden)amino]benzonitrile, 11.5% 2-(4-cyanophenyl)-5-(4-n-butylphenyl)-pyrimidine and 2.5% 5-n-pentyl-2-(4'-cyano-4-biphenylyl)-pyrimidine M.p. < 0° C; Cl.p. 89.0° C.

35.2% p-[(p-n-Butylbenzyliden)amino]benzonitrile, 7.4% p-n-butylbenzoic acid p'-cyanophenyl ester, 7.8% p-n-pentylbenzoic acid p'-cyanophenyl ester, 9.7% p-n-hexylbenzoic acid p'-cyanophenyl ester, 11.4% 5-n-hexyl-2-(4-cyanophenyl)-pyrimidine, 15.2% 5-n-heptyl-2-(4-cyanophenyl)-pyrimidine and 12.8% 2-(4-cyanophenyl)-5-(4-n-butylphenyl)-pyrimidine M.p. < 0° C; Cl.p. 77.5° C.

37.3% p-[(p-n-Butylbenzyliden)amino]benzonitrile, 8.1% p-n-butylbenzoic acid p'-cyanophenyl ester, 8.6% p-n-pentylbenzoic acid p'-cyanophenyl ester, 10.8% p-n-hexylbenzoic acid p'-cyanophenyl ester, 8.9% 5-n-pentyl-2-(4-cyanophenyl)-pyrimidine, 12.5% 5-n-hexyl-2-(4-cyanophenyl)-pyrimidine and 13.5% 2-(4-cyanophenyl)-5-(4-butylphenyl)-pyrimidine M.p. < 3° C; Cl.p. 81.0° C.

36.3% p-[(p-n-Butylbenzyliden)amino]benzonitrile, 7.8% p-n-butylbenzoic acid p'-cyanophenyl ester, 10.2% p-n-hexylbenzoic acid p'-cyanophenyl ester, 12.0% 5-n-hexyl-2-(4-cyanophenyl)-pyrimidine, 16.0% 5-n-heptyl-2-(4-cyanophenyl)-pyrimidine, 13.1% 2-(4-cyanophenyl)-5-(4-n-butylphenyl)-pyrimidine and 4.4% 5-n-hexyl-2-(4'-biphenylyl)-pyrimidine M.p. <0° C; Cl.p. 87.5° C.

12.4% p-[(p-n-Propylbenzyliden)amino]benzonitrile, 33.9% p-[(p-n-butylbenzyliden)amino]benzonitrile, 7.0% p-n-butylbenzoic acid p'-cyanophenyl ester, 9.0% p-n-hexylbenzoic acid p'-cyanophenyl ester, 10.8% 5-n-hexyl-2-(4-cyanophenyl)-pyrimidine, 14.4% 5-n-heptyl-2-(4-cyanophenyl)-pyrimidine and 12.2% 2-(4-cyanophenyl)-5-(4-n-butylphenyl)-pyrimidine M.p. <0° C; Cl.p. 79.0° C.

6.7% p-n-Butylbenzoic acid p'-cyanophenyl ester, 7.1% p-n-pentylbenzoic acid p'-cyanophenyl ester, 8.6% p-n-hexylbenzoic acid p'-cyanophenyl ester, 33.1% p-[(p-n-butylbenzyliden)amino]benzonitrile, 7.4% 5-n-pentyl-2-(4-cyanophenyl)-pyrimidine, 10.4% 5-n-hexyl-2-(4-cyanophenyl)pyrimidine, 13.9% 5-n-heptyl-2-(4-cyanophenyl)pyrimidine and 12.0% 2-(4-cyanophenyl)-5-(4-n-butylphenyl)pyrimidine M.p. <0° C; Cl.p. 77.5° C.

7.4% p-n-Butylbenzoic acid p'-cyanophenyl ester, 7.8% p-n-pentylbenzoic acid p'-cyanophenyl ester, 9.7% p-n-hexylbenzoic acid p'-cyanophenyl ester, 35.2% p-[(p-n-butylbenzyliden)amino]benzonitrile, 11.4% 5-n-hexyl-2-(4-cyanophenyl)pyrimidine, 15.2% 5-n-heptyl-2-(4-cyanophenyl)pyrimidine and 12.8% 2-(4-cyanophenyl)-5-(4-n-butylphenyl)pyrimidine M.p. <0° C; Cl.p. 78.0° C.

9.8% p-[(p-n-Propylbenzyliden)amino]benzonitrile, 28.2% p-[(p-n-butylbenzyliden)amino]benzonitrile, 39.6% p-[(p-n-hexylbenzyliden)amino]benzonitrile, 2.0% 2-(4-cyanophenyl)-5-(4-n-propylphenyl)pyrimidine, 10.3% 2-(4-cyanophenyl)-5-(4-n-butylphenyl)pyrimidine and 9.7% 5-n-butyl-2-(4'-cyano-4-biphenylyl)pyrimidine M.p. <0° C; Cl.p. 105.5° C.

10.3% p-[(p-n-Propylbenzyliden)amino]benzonitrile, 29.3% p-[(p-n-butylbenzyliden)amino]benzonitrile, 41.4% p-[(p-n-hexylbenzyliden)amino]benzonitrile, 9.8% 2-(4-cyanophenyl)-5-(4-n-butylphenyl)pyrimidine and 9.2% 5-n-butyl-2-(4'-cyano-4-biphenylyl)pyrimidine
M.p. <0° C; Cl.p. 100.0° C.

46.8% 4'-n-Pentyl-4-cyanobiphenyl, 23.4% 4'-n-heptyl-4-cyanobiphenyl, 7.8% 4'-heptyloxy-4-cyanobiphenyl, 2.3% 2-(4-cyanophenyl)-5-(4-n-propylphenyl)-pyrimidine, 11.3% 2-(4-cyanophenyl)-5-(4-n-butylphenyl)pyrimidine and 7.7% 4-cyano-4"-n-pentyl-p-terphenyl M.p. <0° C; Cl.p. 85.0° C.

43.9% 4'-n-Pentyl-4-cyanobiphenyl, 21.1% 4'-n-heptyl-4-cyanobiphenyl, 6.7% 4'-n-hexyloxy-4-cyanobiphenyl, 10.6% 2-(4-cyanophenyl)-5-(4-n-butylphenyl)pyrimidine, 9.9% 5-n-butyl-2-(4'-cyano-4-biphenylyl)pyrimidine and 7.2% 4-cyano-4"-n-pentyl-p-terphenyl M.p. <0° C; Cl.p. 98.0° C.

43.6% 4'-n-Pentyl-5-cyanobiphenyl, 20.9% 4'-n-heptyl-4-cyanobiphenyl, 7.6% 4'-n-octyloxy-4-cyanobiphenyl, 10.5% 2-(4-cyanophenyl)-5-(4-n-butylphenyl)-pyrimidine, 9.8% 5-n-butyl-2-(4'-cyano-4-biphenylyl)-pyrimidine and 7.1% 4-cyano-4"-n-pentyl-p-terphenyl M.p. <0° C; Cl.p. 96.0° C.

46.8% 4'-n-Pentyl-4-cyanobiphenyl, 23.4% 4'-n-heptyl-4-cyanobiphenyl, 7.8% 4'-n-heptyloxy-4-cyanobiphenyl, 11.3% 2-(4-cyanophenyl)-5-(4-n-butylphenyl)pyrimidine and 10.6% 5-n-butyl-2-(4'-cyano-4-biphenylyl)pyrimidine M.p. <0° C; Cl.p. 84.5° C.

50.7% 4'-n-Pentyl-4-cyanobiphenyl, 25.4% 4'-n-pentyloxy-4-cyanobiphenyl, 6.0% 5-n-pentyl-2-(4-cyanophenyl)pyrimidine, 8.9% 2-(4-cyanophenyl)-5-(4-n-butylphenyl)pyrimidine and 9.0% 5-n-butyl-2-(4'-cyano-biphenylyl)pyrimidine M.p. <0° C; Cl.p. 83.5° C.

44.8% 4'-n-Pentyl-4-cyanobiphenyl, 21.9% 4'-n-heptyl-4-cyanobiphenyl, 11.7% 5-n-heptyl-2-(4-cyanophenyl)pyrimidine, 10.8% 2-(4-cyanophenyl)-5-(4-n-butylphenyl)pyrimidine and 10.1% 5-n-butyl-2-(4'-cyano-4-biphenylyl)pyrimidine M.p. <0° C; Cl.p. 82.0° C.

46.8% 4'-n-Pentyl-4-cyanobiphenyl, 23.4% 4'-n-heptyl-4-cyanobiphenyl, 7.8% 4'-n-heptyloxy-4-cyanobiphenyl, 11.3% 2-(4-cyanophenyl)-5-(4-n-butylphenyl)pyrimidine and 10.6% 5-n-butyl-2-(4'-cyano-4-biphenylyl)pyrimidine M.p. <0° C; Cl.p. 84.0° C.

8.13% p-[(p-n-Propylbenzyliden)amino]benzonitrile, 24.45% p-[(p-n-butylbenzyliden)amino]benzonitrile, 39.36% p-[(p-n-hexylbenzyliden)amino]benzonitrile, 10.81% p-[5-(p-n-butylphenyl)-2-pyrimidinyl]benzonitrile and 16.75% p-[5-(p-n-pentyloxyphenyl)-2-pyrimidinyl]benzonitrile M.p. <0° C; Cl.p. 112.5° C.

10.2% p-[(p-n-Propylbenzyliden)amino]benzonitrile, 29.1% p-[(p-n-butylbenzyliden)amino]benzonitrile, 40.6% p-[(p-n-hexylbenzyliden)amino]benzonitrile, 9.4% 2-(4-cyanophenyl)-5-(4-n-butylphenyl)pyrimidine and 10.7% 5-(4-cyanophenyl)-2-(4-n-hexylphenyl)-pyrimidine M.p. <0° C; Cl.p. 101.6° C.

The preparation of the compounds of formula I in accordance with the invention and the compounds of formula X is further illustrated by the Examples which follow. All temperatures are given in degrees Centigrade, unless otherwise stated.

EXAMPLE 1

Preparation of 5-(4-n-pentylphenyl)-2-(4-cyanophenyl)-pyrimidine 4.2 g. of 4-[5-(4-n-pentylphenyl)-2-pyrimidyl]-benzoic acid amide are reacted under reflux in a mixture of 200 ml. of ethylene chloride and 2.5 ml. of phosphorus oxychloride for 1 hour, with stirring. The reaction mixture is diluted with ether and washed with 2N sodium hydroxide solution and then with water until neutral. After evaporation of the organic phase, which has been dried over sodium sulfate, 5-(4-n-pentylphenyl)-2-(4-cyanophenyl)-pyrimidine is obtained and is filtered on a short silica gel column and subsequently recrystallized from methylene chloride/methanol, m.p. 125.5°; cl.p. 242.5°-243°.

The starting material can be prepared as follows:

Dry hydrochloric acid gas is passed into a solution of 88.6 g. of 4-cyanobenzoic acid methyl ester in 190 ml. of benzene and 70 ml. of methanol for 3 hours at 0°, with stirring. The reaction mixture is allowed to stand for 5 days at +5° and the imido ether which has precipitated is then removed by filtration. 130 g. of liquid ammonia are added to 178 g. of this crude product, suspended in 300 ml. of methanol, after cooling to about −40° and the mixture is shaken in an autoclave for 24 hours at +70°. After cooling the reaction mixture to room temperature and evaporation of the ammonia, the product which has crystallized out is removed by filtration, and the crystals are washed with hexane and dried overnight at 50° under a water pump vacuum, whereby 4-amidino-benzoic acid amide hydrochloride is obtained.

46.07 g. of 1-(4-n-pentylphenyl)-2-methoxyethylene [Ber. 94, 1373 (1961)] are added dropwise to a solution of 2 ml. of boron trifluoride etherate in 500 ml. of orthoformic acid ethyl ester, cooled in an ice bath, and the reaction mixture is then stirred further at room temperature. After dilution with ether, extraction with 1N sodium hydroxide solution and water and evaporation of the organic phase, dried over sodium sulfate, 4-n-pentylphenyl-malonic tetraacetal is obtained.

7.33 g. of 4-n-pentylphenyl-malonic tetraacetal are stirred overnight in 20 ml. of ethanol with 0.72 ml. of water and two drops of concentrated sulfuric acid at 50° under nitrogen. The acidic pentylphenyl-malonic aldehyde obtained as a byproduct can be separated from the neutral 2-(4-n-pentylphenyl)-3-ethoxyacrolein by shaking out the reaction mixture, diluted with ether, with aqueous sodium carbonate solution.

4.46 g. of 2-(4-n-pentylphenyl)-3-ethoxy-acrolein, 3.63 g. of the 4-amidinobenzoic acid amide hydrochloride described above and 0.0254 mol of sodium methylate (obtained by dissolving 0.584 g. of sodium metal in methanol) are suspended in 250 ml. of methanol and stirred overnight at room temperature under an atmosphere of nitrogen. The yellow suspension is then filtered and the residue is washed with a little ethanol and suspended in 1.4 liters of ether for further purification. The suspension is washed with water and then filtered again. Sparingly soluble 4-[5-(4-n-pentylphenyl)-2-pyrimidinyl]benzoic acid amide is obtained.

The following compounds were prepared in an analogous manner to that described above:

|  | M.P. | Cl.P. |
|---|---|---|
| 5-(4-n-Propylphenyl)-2-(4-cyanophenyl)-pyrimidine | 154–154.5° | 261° |
| 5-(4-n-Butylphenyl)-2-(4-cyanophenyl)-pyrimidine | 94° | 246.0–246.5° |
| 5-(4-n-Hexylphenyl)-2-(4-cyanophenyl)-pyrimidine | 93° | 232.5° |
| 5-(4-n-Heptylphenyl)-2-(4-cyanophenyl)-pyrimidine | 104.5° | 226° |
| 5-(4-Ethylphenyl)-2-(4-cyanophenyl)-pyrimidine | 182° | 262.2° |
| 5-(4-n-Propyloxyphenyl)-2-(4-cyanophenyl)-pyrimidine | 132° | 279.7° |
| 5-(4-n-Butyloxyphenyl)-2-(4-cyanophenyl)-pyrimidine | 119° | 271.6° |
| 5-(4-n-Pentyloxyphenyl)-2-(4-cyanophenyl)-pyrimidine | 85.8° | 261° |
| 5-(4-n-Hexyloxyphenyl)-2-(4-cyanophenyl)-pyrimidine | 94.8° | 254.3° |

EXAMPLE 2

Preparation of 2-(4-n-hexylphenyl)-5-(4-cyanophenyl)-pyrimidine 1.9 g. of 2-(4-n-hexylphenyl)-5-(4-bromophenyl)-pyrimidine are heated to the reflux for 21 hours in 50 ml. of dimethylformamide with 2.5 g. of copper-(I) cyanide (content 70%). After cooling, the reaction mixture is stirred with 25 ml. of 10% strength aqueous ethylenediamine solution and then extracted with methylene chloride. The extract is washed again with aqueous ethylenediamine solution and then several times with water until it gives a neutral reaction. The crude product, obtained after evaporation, is chromatographed on 150 g. of silica gel with toluene/1% acetone. Initially, traces of the starting material are obtained, and then fractions with pure 2-(4-n-hexylphenyl)-5-(4-cyanophenyl)-pyrimidine. After recrystallization from ethyl acetate, the product has a melting point of 121.5° and a clearing point of 250°.

The starting material can be prepared as follows:

A solution of 15 g. of 1-(4-bromophenyl)-2-methoxyethylene [Ber. 94, 1373 (1961)] in 150 ml. of ortho-formic acid ethyl ester is added dropwise at 0°–5° to 5 g. of boron trifluoride etherate in 200 ml. of ortho-formic acid ethyl ester. The mixture is stirred overnight and reaches room temperature. The mixture is then diluted with ether and washed initially with soda solution and then with water until it gives a neutral reaction. The crude product, obtained after evaporation, gives, after recrystallization from hexane, 4-bromophenyl-malonic tetraacetal.

In order to partially hydrolyze this material, 4.5 g. are dissolved in 10 ml. of ethanol, 0.5 ml. of water and 1 drop of concentrated sulfuric acid are added and the mixture is stirred overnight at 50° and then worked up in the usual manner. Crude 2-(4-bromophenyl)-3-ethoxyacrolein is thus obtained and is thereafter used in the crude form.

Initially, 2.5 g. of crude 2-(4-bromophenyl)-3-ethoxyacrolein in 20 ml. of methanol and then 2.4 g. of 4-n-hexylbenzamidine hydrochloride are added to a sodium methylate solution prepared from 0.7 g. of sodium in 25 ml. of methanol. The reaction mixture is heated to the reflux overnight. The solvent is then partially removed by distillation and water is added to the residue and acidified with dilute hydrochloric acid. The resulting precipitate is removed by filtration, washed thoroughly with water and ether and dried. The crude 2-(4-n-hexylphenyl)-5-(4-bromophenyl)-pyrimidine of melting point 152.5°–156° is processed further directly.

The following compounds were prepared in an analogous manner to that described above:

|  | M.P. | Cl.P. |
|---|---|---|
| 2-(4-Ethylphenyl)-5-(4-cyanophenyl)-pyrimidine | 167–167.5° | 279–279.5° |
| 2-(4-n-Propylphenyl)-5-(4-cyanophenyl)-pyrimidine | 167° | 278.5–279° |
| 2-(4-n-Butylphenyl)-5-(4-cyanophenyl)-pyrimidine | 138.5° | 266–266.5° |
| 2-(4-n-Pentylphenyl)-5-(4-cyanophenyl)-pyrimidine | 131.5° | 262.5–263° |
| 2-(4-n-Heptylphenyl)-5-(4-cyanophenyl)-pyrimidine | 121.5° | 245–245.5° |

EXAMPLE 3

Preparation of 5-pentyl-2-(4'-cyano-4-biphenylyl)-pyrimidine 1.5 g. of 5-n-pentyl-2-(4'-bromo-4-biphenylyl)-pyrimidine are heated to the reflux for 22 hours with 2.5 g. of copper-(I) cyanide (content 70%) in 50 ml. of dimethylformamide. After cooling, 25 ml. of 10% strength aqueous ethylenediamine solution are added and, after stirring for a short time, the mixture is extracted with methylene chloride. The organic extract is shaken again with 25 ml. of ethylenediamine solution and then washed until it gives a neutral reaction. The crude concentrate is chromatographed with toluene/1% acetone on silica gel. Recrystallization of the pure fractions from ethyl acetate gives 5-n-pentyl-2-(4'-cyano-4-biphenylyl)-pyrimidine, m.p. 123.5°–124°; cl.p. 204.5°–205°.

The starting material can be prepared as follows:

60.6 g. of titanium tetrachloride are added to 34.5 g. of 4-bromobiphenyl in 164 ml. of methylene chloride at about 2°. 20.7 g. of dichloromethyl methyl ether are added dropwise at the same temperature over a period of 40 minutes. The cooling means is then removed and the mixture is stirred for 21 hours at room temperature. The reaction mixture is poured onto ice and the product is extracted with ether in the usual manner. Chromatography on silica gel with benzene as the eluting agent initially gives unreacted starting material and then 4'-bromo-4-biphenylaldehyde.

Crude oxime is obtained from 17.5 g. of 4'-bromo-4-biphenylaldehyde and 4.4 g. of hydroxylamide hydrochloride in 35 ml. of methanol and 70 ml. of pyridine, after boiling under reflux, which is converted into the nitrile by heating for 15 hours in acetic anhydride. The reaction mixture is concentrated as much as possible on a roller evaporator. The residue is poured onto ice and dilute sodium hydroxide solution and the product is isolated with ether in the usual manner. After treating with hexane, the 4'-bromo-4-cyanobiphenyl melts at about 150°.

Gaseous hydrochloric acid is passed into a mixture of 5.6 g. of 4'-bromo-4-cyanobiphenyl and 1 g. of absolute ethanol in 25 ml. of toluene to saturation. After stirring for 3 days at room temperature, the precipitate is removed by filtration and washed with toluene. The residue is suspended in 5 ml. of absolute ethanol, while still moist, and about 1.3 g. of ammonia are added in the form of a 10% strength ethanolic solution. After stirring for 3 days at room temperature, the 4'-bromo-4-biphenylamidine hydrochloride which has precipitated is separated, washed with ether and dried.

5.8 g. of n-pentyl-malonic tetraacetal are stirred overnight at room temperature in 10 ml. of ethanol with 0.75 ml. of water and 1 drop of concentrated sulfuric acid. The reaction mixture is then diluted with ether, extracted with sodium carbonate solution, washed until neutral and evaporated.

1.42 g. of the crude 2-n-pentyl-3-ethoxyacrolein thus obtained are dissolved in a sodium ethylate solution, obtained from 580 mg. of sodium in 40 ml. of ethanol, and 2.6 g. of the 4'-bromo-4-biphenylamidine hydrochloride described above are added. The mixture is now stirred for 3 days at room temperature. After some of the solvent is removed by distillation, water is added and the mixture is extracted with chloroform in the usual manner. By crystallization from ethanol, 5-n-pentyl2-(4'-4-biphenylyl)-pyrimidine is obtained as needles of melting point 137° and clearing point 197°.

In an analogous manner to that described above, the following compounds were prepared:

5-n-Propyl-2-(4'-cyano-4-biphenylyl)-pyrimidine, m.p. 125.6°; Cl.p. 275.7°;

5-n-Butyl-2-(4'-cyano-4-biphenylyl)-pyrimidine, m.p. 112°; Cl.p. 262°;

5-n-Hexyl-2-(4'-cyano-4-biphenylyl)-pyrimidine, m.p. 108°; Cl.p. 245°;

5-n-Heptyl-2-(4'-biphenylyl)-pyrimidine, m.p. 110°; Cl.p. 241.5°.

EXAMPLE 4

Preparation of
5-cyano-2-(4'-n-hexyl-4-biphenylyl)-pyrimidine 4.31 g. of 2-(4'-n-hexyl-4-biphenylyl)-pyrimidine-5-carboxylic acid amide are boiled for 2 hours under reflux with 75 ml. of phosphorus oxychloride and the excess reagent is removed in vacuo. After this, toluene is added and the mixture is concentrated in vacuo twice. The residue is taken up in methylene chloride and chromatographed on silica gel 60. Methylene chloride/2% acetone elutes 5-cyano-2-(4'-n-hexyl-4-biphenylyl)-pyrimidine, which is recrystallized from acetone/hexane for purification and distilled at 180° in a high vacuum, m.p. 132.5°; cl.p. 258.5° – 259.5°.

The starting material can be prepared as follows:

Hydrochloric acid gas is passed into a solution of 5.0 g. of 4'-n-hexyl-4-cyanobiphenyl in 3.8 ml. of absolute ethanol and 4.8 ml. of absolute benzene for 8 hours, with stirring and cooling to b 0°, and the mixture is allowed to stand overnight at room temperature. After evaporation in vacuo, 100 ml. of absolute ether are added and 4'-n-hexyl-4-biphenyl-imido-ethyl ether hydrochloride is isolated by filtration. The crude salt is suspended in 7.6 ml. of absolute ethanol and stirred for 40 hours with 10.7 g. of a 16% strength (g/g) solution of ammonia in ethanol. The clear reaction solution is evaporated in vacuo and 100 ml. of absolute ether are added. 4-n-Hexyl-4-biphenyl-amidine hydrochloride is isolated by filtration.

A mixture of 6.0 g. of 4'-n-hexyl-4-biphenyl-amidine hydrochloride and 4.9 g. of ethoxymethylene-malonic acid diethyl ester is stirred in a sodium ethylate solution, from 0.867 g. of sodium and 80 ml. of ethanol, for 40 minutes at room temperature and 40 minutes under reflux. After this, the yellow reaction mixture is evaporated in vacuo and the residue is suspended in 95 ml. of water and acidified with 15 ml. of glacial acetic acid. Filtering, washing with water and drying yields crude 2-(4'-n-hexyl-4-biphenylyl)-4-hydroxy-pyrimidine-5-carboxylic acid ethyl ester which can be sublimed at 185° in high vacuum for purification, m.p. 218.0°.

6.95 g. of hydroxypyrimidine are boiled for 1 hour under reflux with 50 ml. of phosphorus oxychloride. The excess reagent is removed by evaporation in vacuo, and the residue is chromatographed in methylene chloride on silica gel 60. Methylene chloride and methylene chloride/2% acetone elute 2-(4'-n-hexyl-4-biphenylyl)-4-chloropyrimidine-5-carboxylic acid ethyl ester, which can be distilled at 180° in high vacuum for purification, m.p. 91.6° – 91.9°, cl.p. 112.6°-112.7°.

6.2 g. of chloropyrimidine are suspended in 300 ml. of ethanol and hydrogenated with 0.4 g. of palladium charcoal (5%) and 2.17 g. of anhydrous potassium acetate at room temperature until 1 mol of hydrogen has been absorbed. The catalyst is separated and rinsed with methylene chloride and the residue is dissolved in benzene, diluted with the equivalent amount of hexane and chromatographed on silica gel 60. Hexane/benzene (1:1) and benzene initially elute a little starting material, then 2-(4'-n-hexyl-4-biphenylyl)-pyrimidine-5-carboxylic acid ethyl ester. The compound can be distilled at 180° in a high vacuum for purification, m.p. 129.2°; cl.p. 181°.

5.12 g. of 2-(4'-n-hexyl-4-biphenylyl)-pyrimidine-5-carboxylic acid ethyl ester are boiled under reflux for 3 hours with 150 ml. of ethanol and 6.1 g. of sodium hydroxide in 45 ml. of water and the reaction mixture is evaporated in vacuo. 50 ml. of water and 100 ml. of 20% strength hydrochloric acid are added to the residue. Filtering, washing with water and drying gives 2-(4'-n-hexyl-4-biphenylyl)-pyrimidine-5-carboxylic acid, which can be converted into the acid chloride by boiling for 2 hours with 30 ml. of thionyl chloride. The excess reagent is removed in vacuo and the residual acid chloride is suspended in 60 ml. of absolute dioxane and added to a solution of 80 ml. of dioxane saturated with ammonia at room temperature, with stirring. Ammonia is passed into the reaction mixture for 4 hours and the mixture is allowed to stand overnight at room temperature. After this, the mixture is evaporated to dryness and the residue is stirred for 30 minutes with 100 ml. of water, filtered, rinsed with water and dried. Colorless 2-(4'-n-hexyl-4-biphenylyl)-pyrimidine-5-carboxylic acid amide is thus obtained, which can be sublimed at 205° in a high vacuum for purification, m.p. >260°.

The following compounds were prepared in an analogous manner to that described above:

5-Cyano-2-(4'-ethyl-4-biphenylyl)-pyrimidine, m.p. 166°; cl.p. 241°;

5-Cyano-2-(4'-n-propyl-4-biphenylyl)-pyrimidine, m.p. 138.7°; Cl.p. 232°;

5-Cyano-2-(4'-n-butyl-4-biphenylyl)-pyrimidine, m.p. 129.3°; Cl.p. 274.6°.

EXAMPLE 5

Preparation of 5-n-heptyl-2-(4-cyanophenyl)-pyrimidine 1.9 g. of 4-(4-n-heptylpyrimid-2-yl)benzoic acid amide are left for 80 minutes under reflux in a mixture of 40 ml. of ethylene chloride and 0.63 ml. of phosphorus oxychloride, with stirring. The reaction mixture, diluted with ether, is washed with 2N sodium hydroxide solution and then with water until neutral. After evaporation of the organic phase, drying over sodium sulfate, 1.9 g. of 5-n-heptyl-2-(4-cyanophenyl)-pyrimidine result, which are distilled in a high vacuum, having a m.p. of 44.2°–44.7°; cl.p. 50.1°–50.4°.

The starting material was prepared as follows:

0.07 mol of 2-n-heptyl-malonic tetraethyl acetal are stirred for 15 hours in 35 ml. of ethanol with 0.14 mol of water and 2 drops of concentrated sulfuric acid at 50° under an atmosphere of nitrogen. The acidic 2-heptyl-malonic aldehyde obtained as a byproduct can be separated from the neutral 2-n-heptyl-3-ethoxyacrolein by shaking out the reaction mixture, diluted with ether, with aqueous sodium carbonate solution.

A suspension consisting of 0.1 mol of 4-amidino-benzoic acid ethyl ester hydrochloride, 0.1 mol of 2-n-heptyl-3-ethoxy-acrolein and 0.14 mol of sodium ethylate in 100 ml. of methanol is stirred overnight at room temperature under an atmosphere of nitrogen. After the usual working up and separation into basic and acidic portions, 4-(4-n-heptylpyrimid-2-yl)-benzoic acid ethyl ester and 4-(4-n-heptylpyrimid-2-yl)benzoic acid are obtained.

A. 30 ml. of liquid ammonia are added to 4.4 g. of 4-(4-n-heptylpyrimid-2-yl)-benzoic acid ethyl ester, dissolved in 50 ml. of a methanol-dichloromethane (1:1) mixture, in an autoclave and the mixture is then warmed to 90° for 5 hours (pressure: 16 atmospheres absolute). The reaction mixture is evaporated to dryness and the more sparingly soluble amide is separated from unreacted educt, whereby 4-(4-n-heptylpyrimid-2-yl)-benzoic acid amide is obtained.

B. 2.3 g. of 4-(4-n-heptylpyrimid-2-yl)benzoic acid and 1.9 ml. of thionyl chloride are left in 100 ml. of benzene for 8 hours under reflux and the reaction mixture is then evaporated to dryness on a vacuum film evaporator. The resulting residue is dissolved in 50 ml. of dichloromethane and ammonia is passed into the solution at room temperature for 2 hours. 4-(4-Heptylpyrimid-2-yl)benzoic acid amide is obtained in virtually quantitative yield.

EXAMPLE 6

Preparation of 5-n-hexyl-2-(4-cyanophenyl)-pyrimidine 15.58 g. of 4-(4-n-hexylpyrimid-2-yl)benzoic acid amide are left in a mixture of 350 ml. of ethylene chloride and 5.58 ml. of phosphorus oxychloride for 90 minutes under reflux, with stirring. The reaction mixture, diluted with ether, is washed with 2N sodium hydroxide solution and then with water until neutral. After evaporation of the organic phase, drying over sodium sulfate, 14.6 g. of 5-n-hexyl-2-(4-cyanophenyl)pyrimidine result, which are distilled in high vacuum, m.p. 53.5° – 54.5°; cl.p. 35.5° – 36.5°.

The starting material was prepared as follows:

0.1 mol of 2-n-hexyl-malonic tetraethyl acetal are stirred for 18 hours in 40 ml. of ethanol with 0.2 mol of water and 3 drops of concentrated sulfuric acid at 50° under an atmosphere of nitrogen. The acidic 2-hexyl-malonic aldehyde obtained as a byproduct can be separated from the neutral 2-n-hexyl-3-ethoxyacrolein by shaking out the reaction mixture, dilution with ether and with aqueous sodium carbonate solution.

60 ml. of liquid ammonia are added to 89 g. of 4-methyl-imido-benzoic acid methyl ester hydrochloride, suspended in 150 ml. of methanol, at −40°, the resulting suspension is transferred to an autoclave, compressed to 30 atmospheres of nitrogen and left for 24 hours at 70°. The product which crystallizes out is filtered, washed with hexane and dried at 40° under vacuum (14 mm). 72 g. of 4-amidino-benzoic acid amide hydrochloride are obtained.

0.082 mol of 4-amidino-benzoic acid amide hydrochloride, suspended in a solution of 0.082 mol of 2-n-hexyl-3-ethoxy-acrolein and 0.14 mol of sodium methylate in 150 ml. of methanol, are stirred overnight at room temperature under an atmosphere of nitrogen. The precipitate obtained by diluting the reaction mixture with 3.1 of ether is removed by filtration, washed with water until neutral and dried at 40° in a vacuum drying cabinet, whereby 17.9 g. of 4-(4-n-hexylpyrimid-2-yl)benzoic acid amide are obtained, m.p. 231.6° – 233.0°.

EXAMPLE 7

Preparation of 2-(p-n-pentylphenyl)-5-pyrimidinecarboxylic acid ethyl ester

A mixture of 12.6 g. of 2-(p-n-pentylphenyl)-4-chloro-5-pyrimidinecarboxylic acid ethyl ester, 1.1 g. of palladium charcoal (5%), 5.6 g. of potassium acetate (anhydrous) and 156 ml. of ethanol is hydrogenated at room temperature until 1 mol. of hydrogen has been absorbed (time 1 hour). The catalyst is removed by filtration. The filtrate is evaporated in vacuo and any starting material present is separated by chromatography on silica gel (solvent benzene and benzene/2% acetone). The pure colorless 2-(p-n-pentylphenyl)-5-pyrimidinecarboxylic acid ethyl ester obtained melts, after distillation at 130° in high vacuum (bulb tube), at 85.1° – 86.7°.

10.2 g. of 2-(p-n-pentylphenyl)-5-pyrimidinecarboxylic acid ethyl ester are boiled under reflux with a solution of 15.8 g. of sodium hydroxide in 105 ml. of water, after adding 21 ml. of ethanol, for 1 hour. After cooling, the mixture is made congo-acid with 82 ml. of 20% strength hydrochloric acid. The 2-(p-n-pentylphenyl)-5-pyrimidinecarboxylic acid which has precipitated is separated, washed with water, dried and reacted further in the crude form.

9.3 g. of 2-(p-n-pentylphenyl)-5-pyrimidinecarboxylic acid are boiled under reflux, with the exclusion of moisture with 50 ml. of thionyl chloride for 2 hours. The excess reagent is removed in vacuo. The residual 2-(p-n-pentylphenyl)-5-pyrimidinecarboxylic acid chloride is dissolved in 100 ml. of absolute dioxane and added to a solution of 200 ml. of absolute dioxane saturated with ammonia at room temperature, with stirring, and a colorless precipitate forms. After this, ammonia is passed into the reaction mixture for an additional 4 hours. The resulting mixture is allowed to stand overnight at room temperature. Thereafter, it is evaporated in vacuo and the residue is stirred with 100 ml. of water for 30 minutes. The precipitate is separated, washed with water and dried. The resulting crude 2-(p-n-pentylphenyl)-5-pyrimidinecarboxamide is processed further directly.

9.1 g. of 2-(p-n-pentylphenyl)-5-pyrimidinecarboxamide are boiled under reflux, with the exclusion of moisture, with 100 ml. of phosphorus oxychloride for 2 hours. After this, the excess reagent is removed in vacuo, and the mixture is evaporated again twice with toluene in vacuo. The residue is taken up in methylene chloride and chromatographed on 100 g. of silica gel in methylene chloride. Methylene chloride and methylene chloride/2% acetone elute 5-cyano-2-(4-n-pentylphenyl)-pyrimidine, which is recrystallized from acetone/hexane and sublimed at 120° in a high vacuum to constant melting point. The pure colorless product melts at 96.0°-96.2° and has a clearing point of 109.0°.

The starting material can be obtained according to the data by A. R. Todd and F. Bergel, J. Chem. Soc, 1937, 366 from p-n-pentylbenzamidine hydrochloride and ethoxymethylenemalonic acid diethyl ester with sodium ethylate in ethanol and subsequent treatment of the resulting 2-(p-n-pentylphenyl)-4-hydroxy-5-pyrimidinecarboxylic acid ethyl ester (melting point 193.9°-194.4°) with phosphorus oxychloride, m.p. 58.5°-59.2°.

EXAMPLE 8

Preparation of 2-(p-n-hexylphenyl)-5-pyrimidinecarboxylic acid ethyl ester

A mixture of 15.6 g. of 2-(p-n-hexylphenyl)-4-chloro-5-pyrimidinecarboxylic acid ethyl ester, 1.3 g. of palladium charcoal (5%), 6.7 g. of potassium acetate (anhydrous) and 150 ml. of dioxane is hydrogenated at room temperature until 1 mol of hydrogen has been absorbed (time 70 hours). The reaction mixture is worked up as in Example 7. The pure colorless 2-(p-n-hexylphenyl)-5-pyrimidinecarboxylic acid ethyl ester obtained melts, after distillation at 125° in a high vacuum, at 83.2°-83.9°.

14.1 g. of 2-(p-n-hexylphenyl)-5-pyrimidinecarboxylic acid ethyl ester are reacted with a solution of 20.8 g. of sodium hydroxide in 140 ml. of water, after adding 28 ml. of ethanol, as in Example 7 and worked up. The dry 2-(p-n-hexylphenyl)-5-pyrimidinecarboxylic acid is reacted further in the crude form.

12.0 g. of 2-(p-n-hexylphenyl)-5-pyrimidinecarboxylic acid are reacted, with the exculsion of moisture with 80 ml. of thionyl chloride as in Example 7 and worked up. The residual 2-(p-n-hexylphenyl)-5-pyrimidinecarboxylic acid chloride is dissolved in 120 ml. of absolute dioxane, with warming, and adding to a solution of 200 ml. of absolute dioxane saturated with ammonia at room temperature, with stirring. The mixture is then treated as in Example 7 and worked up. A sample of the resulting crude 2-(p-n-hexylphenyl)-5-pyrimidinecarboxamide is sublimed at 180° in a high vacuum for purification, m.p. 250.2°-258.3°.

11.5 g. of 2-(p-n-hexylphenyl)-5-pyrimidinecarboxamide are reacted, with the exclusion of moisture, with 100 ml. of phosphorus oxychloride as in Example 7, worked up and purified. The pure colorless 5-cyano--2-(4-n-hexylphenyl)pyrimidine melts at 86.3°-87.8° (smectic), becomes nematic at 101.3° and has a clearing point of 102.6°-103.2°.

The starting material can be obtained according to the procedure described by A. R. Todd and F. Bergel, J. Chem. Soc. 1937, 366 from p-n-hexylbenzamidine hydrochloride and ethoxymethylenemalonic acid diethyl ester with sodium ethylate in ethanol and subsequent treatment of the resulting 2-(p-n-hexylphenyl)-4-hydroxy-5-pyrimidinecarboxylic acid ethyl ester (m.p. 189.6°-191.0°) with phosphorus oxychloride, m.p. 59.4°-60.5°.

We claim:
1. A compound of the formula

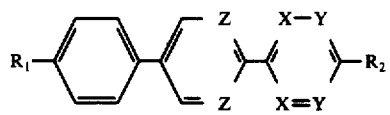

wherein wher X is nitrogen, Y and Z are —CH—; or when Y is nitrogen, X and Z are —CH—; or when Z is nitrogen, X and Y are —CH—; and one of $R_1$ and $R_2$ is cyano and the other is straight-chain alkyl of 1 to 7 carbon atoms, straight-chain alkoxy of 1 to 7 carbon atoms or straight-chain alkanoyloxy of 2 to 7 carbon atoms.

2. A compound in accordance with claim 1, wherein one of $R_1$ and $R_2$ is cyano and the other is straight-chain alkyl of 3 to 7 carbon atoms.

3. A compound in accordance with claim 2, wherein $R_2$ is cyano.

4. A compound in accordance with claim 2, wherein Y is —CH—.

5. A compound in accordance with claim 2, wherein Z is nitrogen.

6. A compound in accordance with claim 1, wherein one of $R_1$ and $R_2$ is cyano and the other is straight-chain alkyl of 3 to 7 carbon atoms and Z is nitrogen and X and Y are —CH—.

7. A compound in accordance wit claim 1, 5-(-4-n-pentylphenyl)-2-(4-cyanophenyl)-pyrimidine.

8. A compound in accordance with claim 1, 5-(4-n-propylphenyl)-2-(4-cyanophenyl)-pyrimidine.

9. A compound in accordance with claim 1, 5-(4-n-butylphenyl)-2-(4-cyanophenyl)-pyrimidine.

10. A compound in accordance with claim 1, 5-(4-n-hexylphenyl)-2-(4-cyanophenyl)-pyrimidine.

11. A compound in accordance with claim 1, 5-(4-n-heptylphenyl)-2-(4-cyanophenyl)-pyrimidine.

12. A compound in accordance with claim 1, 2-(4-n-hexylphenyl)-5-(4-cyanophenyl)-pyrimidine.

13. A compound in accordance with claim 1, 2-(4-ethylphenyl)-5-(4-cyanophenyl)-pyrimidine.

14. A compound in accordance with claim 1, 2-(4-n-propylphenyl)-5-(4-cyanophenyl)-pyrimidine.

15. A compound in accordance with claim 1, 2-(4-n-butylphenyl)-5-(4-cyanophenyl)-pyrimidine.

16. A compound in accordance with claim 1, 2-(4-n-pentylphenyl)-5-(4-cyanophenyl)-pyrimidine.

17. A compound in accordance with claim 1, 2-(4-n-heptylphenyl)-5-(4-cyanophenyl)-pyrimidine.

18. A compound in accordnace with claim 1, 5-n-pentyl-2-(4'-cyano-4-biphenylyl)-pyrimidine.

19. A compound in accordance with claim 1, 5-cyano-2-(4'-n-hexyl-4-biphenylyl)-pyrimidine.

20. A compound in accordance with claim 1, 5-cyano-2-(4'-ethyl-4-biphenylyl)-pyrimidine.

21. A compound in accordance with claim 1, 5-(4-ethylphenyl)-2-(4-cyanophenyl)-pyrimidine.

22. A compound in accordance with claim 1, 5-(4-n-propyloxyphenyl)-2-(4-cyanophenyl)-pyrimidine.

23. A compound in accordance with claim 1, 5-(4-n-butyloxyphenyl)-2-(4-cyanophenyl)-pyrimidine.

24. A compound in accordance with claim 1, 5-(4-n-pentyloxyphenyl)-2-(4-cyanophenyl)-pyrimidine.

25. A compound in accordance with claim 1, 5-(4-n-hexyloxyphenyl)-2-(4-cyanophenyl)-pyrimidine.

26. A compound in accordance with claim 1, 5-n-propyl-2-(4'-cyano-4-biphenylyl)-pyrimidine.

27. A compound in accordnace with claim 1, 5-n-butyl-2-(4'-cyano-4-biphenylyl)-pyrimidine.

28. A compound in accordance with claim 1, 5-n-hexyl-2-(4'-cyano-4-biphenylyl)-pyrimidine.

29. A compound in accordance with claim 1, 5-n-heptyl-2-(4'-cyano-4-biphenylyl)-pyrimidine.

30. A compound in accordance with claim 1, 5-cyano-2-(4'-n-propyl-4-biphenylyl)-pyrimidine.

31. A compound in accordance with claim 1, 5-cyano-2-(4'-n-butyl-4-biphenylyl)-pyrimidine.

32. A nematic composition for electro-optical display cells, which comprises one or more compounds of the formula

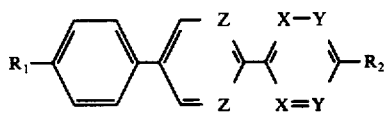

wherein when X is nitrogen, Y and Z are —CH—; or when Y is nitrogen, X and Z are —CH—; or when Z is nitrogen, X and Y are —CH—; and one of $R_1$ and $R_2$ is cyano and the other is straight-chain alkyl of 1 to 7 carbon atoms, straight-chain alkoxy of 1 to 7 carbon atoms or straight-chain alkanoyloxy of 2 to 7 carbon atoms, and one or more nematic compounds having a positive anisotropy.

33. A nematic composition in accordance with claim 32, comprising p-[(p-n-butylbenzyliden)amino]benzonitrile, p-n-butylbenzoic acid p'-cyanophenyl ester, p-n-pentylbenzoic acid p'-cyanophenyl ester, p-n-hexylbenzoic acid p'-cyanophenyl ester, 5-n-pentyl-2-(4-cyanophenyl)-pyrimidine, 5-n-heptyl-2-(4-cyanophenyl)-pyrimidine and 2-(4-cyanophenyl)-5-(4-n-butylphenyl)-pyrimidine.

34. A nematic composition in accordance with claim 32, comprising p-n-butylbenzoic acid p'-cyanophenyl ester, p-n-pentylbenzoic acid p'-cyanophenyl ester, p-n-hexylbenzoic acid p'-cyanophenyl ester, p-n-heptylbenzoic acid p'-cyanophenyl ester, 5-n-pentyl-2-(4-cyanophenyl)-pyrimidine, 5-n-heptyl-2-(4-cyanophenyl)-pyrimidine and 2-(4-cyanophenyl)-5-(4-n-butylphenyl)-pyrimidine.

35. A nematic composition in accordance with claim 32, comprising p-[(p-n-propylbenzyliden)amino]benzonitrile, p-[(p-n-butylbenzylidene)amino]benzonitrile, p-[(p-n-hexylbenzyliden)amino]benzonitrile, 5-cyano-2-(4-n-hexylphenyl)-pyrimidine, 5-n-heptyl-2-(4-cyanophenyl)-pyrimidine, 2-(4-cyanophenyl)-5-(4-n-propylphenyl)-pyrimidine, 2-(4-cyanophenyl)-5-(4-n-butylphenyl)-pyrimidine and 2-(4-cyanophenyl)-5-(4-n-hexylphenyl)-pyrimidine.

36. A nematic composition in accordance with claim 32, comprising p-[(p-n-propylbenzyliden)amino]benzonitrile, p-(p-n-propylbenzyliden)amino]benzonitrile, p-[(p-n-hexylbenzyliden)amino]benzonitrile, 5-cyano-2-(4'-n-propyl-4-biphenylyl)-pyrimidine, 2-(4-cyanophenyl)-5-(4-n-butylphenyl)-pyrimidine and 5-n-pentyl-2-(4'-cyano-4-biphenylyl)-pyrimidine.

37. A nematic composition in accordance with claim 32, comprising p-[(p-n-propylbenzyliden)amino]benzonitrile, p-[(p-n-butylbenzyliden)amino]benzonitrile, p-[p-n-hexylbenzyliden)amino]benzonitrile, 5-cyano-2-(4-n-pentylphenyl)-pyrimidine, 5-cyano-2-(4-n-butyloxyphenyl)-pyrimidine, 5-cyano-2-(4-n-valeryloxyphenyl)-pyrimidine, 2-(4-cyanophenyl)-5-(4-n-propylphenyl)-pyrimidine and 2-(4-cyanophenyl)-5-(4-n-butylphenyl)-pyrimidine.

38. A nematic composition in accordance with claim 32, comprising p-[(p-n-propylbenzyliden)-amino]benzonitrile, p-](p-n-butylbenzyliden)amino]benzonitrile, p-](p-n-hexylbenzyliden)amino]benzonitrile, 2-(4-cyanophenyl)-5-(4-n-butylphenyl)pyrimidine and 5-n-butyl-2-(4'-cyano-4-biphenylyl)-pyrimidine.

39. A nematic composition in accordance with claim 32, comprising 4'-n-pentyl-4-cyanobiphenyl, 4'-n-pentyloxy-4-cyanobiphenyl, 5-n-pentyl-2-(4-cyanophenyl)-pyrimidine, 2-(4-cyanophenyl)-5-(4-n-butylphenyl)-pyrimidine and 5-n-butyl-2-(4'-cyano-4-biphenylyl)-pyrimidine.

40. A nematic composition in accordance with claim 32, comprising p-[(p-n-propylbenzyliden)amino]benzonitrile, p-[(p-n-butylbenzyliden)amino]benzonitrile, p-n-butylbenzoic acid p'-cyanophenyl ester, p-n-hexylbenzoic acid p'-cyanophenyl ester, 5-n-pentyl-2-(4-cyanophenyl)-pyrimidine, 5-n-hexyl-2-(4-cyanophenyl)-pyrimidine, 5-n-heptyl-2-(4-cyanophenyl)-pyrimidine and 2-(4-cyanophenyl)-5-(4-n-butylphenyl)-pyrimidine.

41. A nematic composition in accordance with claim 32, comprising (p-[(p-n-propylbenzyliden)amino]benzonitrile, p-[(p-n-butylbenzyliden)amino]benzonitrile, p-[p-n-hexylbenzyliden) amino]benzonitrile, p-[5-(p-n-butylphenyl)-2-pyrimidinyl]benzonitrile and p-[5-(p-n-pentyloxyphenyl)-2-pyrimidinyl]benzonitrile.

42. A nematic composition in accordance with claim 32, comprising p-[(p-n-propylbenzyliden)amino]benzonitrile, p-[(p-n-butylbenzyliden)amino]benzonitrile, p-[(p-n-hexylbenzyliden) amino]benzonitrile, 2-(4-cyanophenyl)-5-(4-n-butylphenyl)pyrimidine and 5-(4-cyanophenyl)-2-(4-n-hexylphenyl)pyrimidine.

43. A nematic composition which comprises at least one pyrimidine derivative of the formula

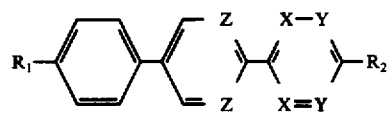

wherein when X is nitrogen, Y and Z are —CH—; or when Y is nitrogen, X and Z are —CH—; or when Z is nitrogen, X and Y are —CH—; and one of $R_1$ and $R_2$ is cyano and the other is straight-chain alkyl of 1 to 7 carbon atoms, straight-chain alkoxy of 1 to 7 carbon atoms or straight-chain alkanoyloxy of 2 to 7 carbon atoms, and at least one compound of the formula

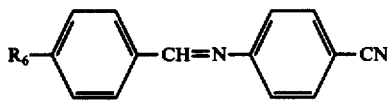

wherein R₆ is straight-chain alkyl of 2 to 8 carbon atoms, straight-chain alkoxy of 4 to 7 carbon atoms, straight-chain alkanoyloxy of 2 to 8 carbon atoms or straight-chain alkylcarbonate of 2 to 11 carbon atoms.

44. A nematic composition which comprises at least one pyrimidine derivative of the formula

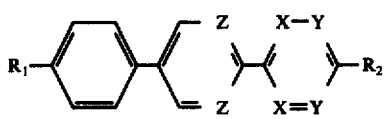

wherein when X is nitrogen, Y and Z are —CH—; or when Y is nitrogen, X and Z are —CH—; or when Z is nitrogen, X and Y are —CH—; and one of $R_1$ and $R_2$ is cyano and the other is straight-chain alkyl of 1 to 7 carbon atoms, straight-chain alkoxy of 1 to 7 carbon atoms or straight-chain alkanoyloxy of 2 to 7 carbon atoms, and at least one compound of the formula

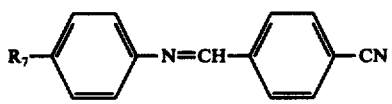

wherein $R_7$ is straight-chain alkyl of 4 to 7 carbon atoms or straight-chain alkycarbonate of 2 to 11 carbon atoms.

45. A nematic composition which comprises at least one pyrimidine derivative of the formula

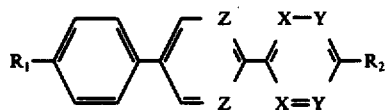

wherein when X is nitrogen, Y and Z are —CH—; or when Y is nitrogen, X and Z are —CH—; or when Z is nitrogen, X and Y are —CH—; and one of $R_1$ and $R_2$ is cyano and the other is straight-chain alkyl of 1 to 7 carbon atoms, straight-chain alkoxy of 1 to 7 carbon atoms or straight-chain alkanoyloxy of 2 to 7 carbon atoms, and at least one compound of the formula

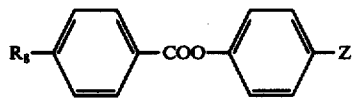

wherein Z is cyano, straight-chain alkyl of 1 to 9 carbon atoms, straight-chain alkoxy of 1 to 9 carbon atoms or straight-chain alkanoyloxy of 1 to 10 carbon atoms and $R_8$ is straight-chain alkyl of 4 to 8 carbon atoms, straight-chain alkoxy of 5 to 8 carbon atoms, straight-chain alkanoyloxy of 2 to 8 carbon atoms or straight-chain alkylcarbonate of 3 to 11 carbon atoms.

46. A nematic composition which comprises at least one pyrimidine derivative of the formula

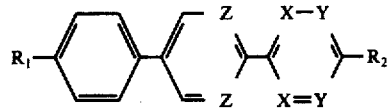

wherein when X is nitrogen, Y and Z are —CH—; or when Y is nitrogen, X and Z are —CH—; or when Z is nitrogen, X and Y are —CH—; and one of $R_1$ and $R_2$ is cyano and the other is straight-chain alkyl of 1 to 7 carbon atoms, straight-chain alkoxy of 1 to 7 carbon atoms or straight-chain alkanoyloxy of 2 to 7 carbon atoms, and at least one compound of the formula

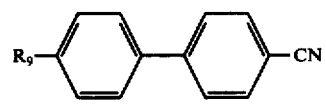

wherein $R_9$ is straight-chain alkyl of 4 to 8 carbon atoms, straight-chain alkoxy of 4 to 8 carbon atoms, straight-chain alkanoyloxy of 4 to 9 carbon atoms or straight-chain alkylcarbonate of 4 to 11 carbon atoms.

47. A nematic composition which comprises at least one pyrimidine derivative of the formula

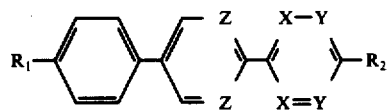

wherein when X is nitrogen, Y and Z are —CH—; or when Y is nitrogen, X and Z are —CH—; or when Z is nitrogen, X and Y are —CH—; and one of $R_1$ and $R_2$ is cyano and the other is straight-chain alkyl of 1 to 7 carbon atoms, straight-chain alkoxy of 1 to 7 carbon atoms or straight-chain alkanoyloxy of 2 to 7 carbon atoms, and at least one compound of the formula

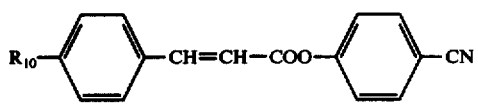

wherein $R_{10}$ is straight-chain alkyl of 1 to 8 carbon atoms.

48. A nematic composition which comprises at least one pyrimidine derivative of the formula

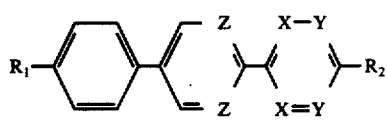

wherein when X is nitrogen, Y and Z are —CH—; or when Y is nitrogen, X and Z are —CH—; or when Z is nitrogen, X and Y are —CH—; and one of $R_1$ and $R_2$ is cyano and the other is straight-chain alkyl of 1 to 7 carbon atoms, straight-chain alkoxy of 1 to 7 carbon atoms or straight-chain alkanoyloxy of 2 to 7 carbon atoms, and at least one compound of the formula

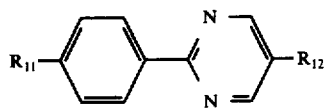

wherein one of $R_{11}$ and $R_{12}$ is cyano and the other is straight-chain alkyl of 3 to 9 carbon atoms, straight-chain alkoxy of 2 to 9 carbon atoms or straight-chain alkanoyloxy of 2 to 9 carbon atoms.

49. An electro-optical display cell comprising liquid crystal means comprising one or more compounds selected from the group consisting of compounds of the formula

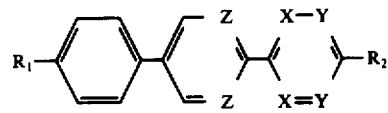

wherein when X is nitrogen, Y and Z are —CH—; or when Y is nitrogen, X and Z are —CH—; or when Z is nitrogen, X and Y are —CH—; and one of $R_1$ and $R_2$ is cyano and the other is straight-chain alkyl of 1 to 7 carbon atoms, straight-chain alkoxy of 1 to 7 carbon atoms or straight-chain alkanoyloxy of 2 to 7 carbon atoms, and one or more nematic compounds having a positive anisotropy.

* * * * *

UNITED STATES PATENT AND TRADEMARK OFFICE
CERTIFICATE OF CORRECTION

PATENT NO. : 4,062,798
DATED : December 13, 1977
INVENTOR(S) : Arthur Boller et al.

It is certified that error appears in the above-identified patent and that said Letters Patent are hereby corrected as shown below:

Column 31, claim 35, line 60, "p-[(p-n-butylbenzylidene)amino] benzonitrile" should be:

p-[(p-n-butylbenzyliden)amino] benzonitrile

Column 32, claim 36, line 1, "p-(p-n-propylbenzyliden)amino] " should be:

p-[(p-n-propylbenzyliden)amino]

Column 32, claim 37, line 10, "p-[p-n-hexylbenzyliden)amino] " should be:

p-[(p-n-hexylbenzyliden)amino]

Column 32, claim 38, line 19, "p-] (p-n-butylbenzyliden)amino] " should be:

p-[(p-n-butylbenzyliden)amino]

UNITED STATES PATENT AND TRADEMARK OFFICE
CERTIFICATE OF CORRECTION

PATENT NO. : 4,062,798  
DATED : December 13, 1977  
INVENTOR(S) : Arthur Boller et al.

It is certified that error appears in the above—identified patent and that said Letters Patent are hereby corrected as shown below:

Column 32, claim 38, line 20, "p-] (p-n-hexylbenzyliden)amino]" should be:

p-[(p-n-hexylbenzyliden)amino]

Column 32, claim 41, line 41, "(p-[(p-n-propylbenzyliden)amino]" should be:

p-[(p-n-propylbenzyliden)amino]

Column 32, claim 41, line 43, "p-[p-n-hexylbenzyliden)amino]" should be:

p-[(p-n-hexylbenzyliden)amino]

Signed and Sealed this

Fourth Day of July 1978

[SEAL]

Attest:

RUTH C. MASON  
Attesting Officer

DONALD W. BANNER  
Commissioner of Patents and Trademarks